(12) United States Patent
McKenna et al.

(10) Patent No.: US 9,740,819 B2
(45) Date of Patent: Aug. 22, 2017

(54) METHOD FOR DETERMINING RISK OF DIABETES

(75) Inventors: Michael P. McKenna, Branford, CT (US); Michael Rowe, Oakland, CA (US); Edward J. Moler, Jr., Walnut Creek, CA (US); Robert W. Gerwien, Newington, CT (US)

(73) Assignee: TRUE HEALTH IP LLC, Frisco, TX (US)

(*) Notice: Subject to any disclaimer, the term of this patent is extended or adjusted under 35 U.S.C. 154(b) by 975 days.

(21) Appl. No.: 13/504,478

(22) PCT Filed: Oct. 28, 2010

(86) PCT No.: PCT/US2010/054397
§ 371 (c)(1),
(2), (4) Date: Aug. 15, 2012

(87) PCT Pub. No.: WO2011/059720
PCT Pub. Date: May 19, 2011

(65) Prior Publication Data
US 2012/0309030 A1    Dec. 6, 2012

Related U.S. Application Data

(60) Provisional application No. 61/256,286, filed on Oct. 29, 2009.

(51) Int. Cl.
G01N 33/48    (2006.01)
G01N 31/00    (2006.01)
G06F 13/10    (2006.01)
G06F 19/24    (2011.01)
G06F 19/18    (2011.01)

(52) U.S. Cl.
CPC .............. *G06F 19/24* (2013.01); *G06F 19/18* (2013.01)

(58) Field of Classification Search
CPC .... A61K 2300/00; A61K 45/06; A61K 33/00; G01N 33/6893; G01N 2800/042; G01N 2800/50
See application file for complete search history.

(56) References Cited

U.S. PATENT DOCUMENTS

| | | | |
|---|---|---|---|
| 4,230,797 | A | 10/1980 | Boguslaski et al. |
| 4,233,402 | A | 11/1980 | Maggio et al. |
| 4,275,149 | A | 6/1981 | Litman et al. |
| 4,376,110 | A | 3/1983 | David et al. |
| 4,659,678 | A | 4/1987 | Forrest et al. |

(Continued)

OTHER PUBLICATIONS

American Diabetes Association, Diagnosis and classification of diabetes mellitus, Diabetes Care, 32(Suppl 1):S62-7 (2009).

(Continued)

*Primary Examiner* — Larry D Riggs, II
(74) *Attorney, Agent, or Firm* — Perkins Coie LLP

(57) ABSTRACT

A method of determining risk of diabetes is provided. In one embodiment, the method comprises: a) measuring the levels of a plurality of biomarkers in a blood samples obtained from a patient, wherein the plurality of biomarkers comprises at least five of the following biomarkers: glucose, adiponectin, CRP, IL2RA, ferritin, insulin and HbAlc; b) calculating a diabetes risk score for the patients using the levels and, optionally, patient age and/or gender. Results obtained from performing the assay on a reference population are similar or identical to those obtained using Formula I.

11 Claims, 2 Drawing Sheets

Descriptive Statistics

Table 8.4: Descriptive Statistics of the DRS Score

| | | Algorithm A | |
|---|---|---|---|
| | | Converter | Non-Converter |
| Training | | | |
| | Mean | 6.79 | 3.31 |
| | SD | 2.35 | 2.475 |
| | Median | 7.63 | 2.67 |
| | IQR | 5.14-8.52 | 1.21-4.98 |
| | N | 100 | 299 |
| Validation | | | |
| | Mean | 6.76 | 3.42 |
| | SD | 2.22 | 2.42 |
| | Median | 7.16 | 2.88 |
| | IQR | 5.46 - 8.61 | 1.35 - 5.08 |
| | N | 102 | 298 |

(56) References Cited

U.S. PATENT DOCUMENTS

| | | | |
|---|---|---|---|
| 4,727,022 | A | 2/1988 | Skold et al. |
| 5,018,067 | A | 5/1991 | Mohlenbrock et al. |
| 7,723,050 | B2 | 5/2010 | Urdea et al. |
| 8,119,358 | B2 | 2/2012 | Urdea et al. |
| 8,409,816 | B2 | 4/2013 | Urdea et al. |
| 2002/0038227 | A1 | 3/2002 | Fey et al. |
| 2004/0122296 | A1 | 6/2004 | Hatlestad et al. |
| 2004/0122297 | A1 | 6/2004 | Stahmann et al. |
| 2007/0218519 | A1 | 9/2007 | Urdea et al. |
| 2007/0259377 | A1 | 11/2007 | Urdea et al. |
| 2009/0012716 | A1 | 1/2009 | Urdea et al. |
| 2012/0328594 | A1 | 12/2012 | McKenna et al. |

OTHER PUBLICATIONS

American Diabetes Association, Diagnosis and classification of diabetes mellitus, Diabetes Care, 33(Suppl 1):S62-9 (2010).

Cook, Use and misuse of the receiver operating characteristic curve in risk prediction, Circulation, 115(7):928-35 (2007).

Corder, Nonparametric Statistics for Non-Statisticians: A Step-by-Step Approach, Wiley (2009).

Definition, Diagnosis and Classification of Diabetes Mellitus and its Complications, Part I, World Health Organization (1999).

Johnson et al., Continuous Univariate Distributions, 2nd ed., vol. 1, Chapter 18, John Wiley and Sons (1994).

Kisner, Product development: the making of the Abbott Architect, Clin. Lab Manage Rev., 11(6):419-21 (1997).

Maggio, Enzyme-Immunoassay, Boca Raton: CRC Press (1980).

Mood et al., Introduction to the Theory of Statistics, 3rd ed., pp. 241-246, McGraw-Hill (1974).

National Institute of Standards and Technology, Engineering Statistics Handbook (2006).

O'Marcaigh et al., Estimating the predictive value of a diagnostic test. How to prevent misleading or confusing results, Clin. Pediatr. (Phila.), 32(8):485-91 (1993).

Ognibene et al., A new modular chemiluminescence immunoassay analyser evaluated, Clin. Chem. Lab. med., 38(3):251-60 (2000).

Park et al., Three-year experience in using total laboratory automation system, Southeast Asian J. Trop. Med. Public Health, 33 Suppl. 2: 68-73 (2002).

Pauli et al., The Abbott Architect c8000: analytical performance and productivity characteristics of a new analyzer applied to general chemistry testing, Clin. Lab., 51(1-2):31-41 (2005).

Pepe et al., Limitations of the odds ratio in gauging the performance of a diagnostic, prognostic, or screening marker, Am. J. Epidemiol., 159(9):882-90 (2004).

Schultz, Clinical interpretation of laboratory procedures, chapter 14 pp. 192-199, In: Burtis et al. (eds.), Teitz,Fundamentals of Clinical Chemistry, 4th ed., W.B. Saunders (1996).

Spearman, The proof and measurement of association between two things, Int. J. Epidemiology, 39:1137-50 (2010).

Vasan, Biomarkers of cardiovascular disease: molecular basis and practical considerations, Circulation, 113(19):2335-62 (2006).

Wilson et al., Clinical Chemistry Analyzer Sub-System Level Performance, American Association for Clinical Chemistry Annual Meeting, Chicago, Illinois, Jul. 23-27, 2008.

Wirth et al., Post-transitional modification detection using metastable ions in reflector matrix-assisted laser desoption/ionization-time of flight mass spectrometry, Proteomics, 2:1445-51 (2002).

Zelen et al., Probability functions, chapter 26 in: Abramowitz et al. (eds.), Handbook of Mathematical Functions with Formulas, Graphs, and Mathematical Tables, National Bureau of Standards, Applied Mathematics Series (1964).

Zweig et al., ROC curve analysis: an example showing the relationships among serum lipid and apolipoprotein concentrations in identifying subjects with coronary artery disease, Clin. Chem., 38(8):1425-8 (1992).

International Search Report and Written Opinion for corresponding international application No. PCT/US2010/054397.

Descriptive Statistics

Table 8.4: Descriptive Statistics of the DRS Score

|  |  | Algorithm A | |
|---|---|---|---|
|  |  | Converter | Non-Converter |
| Training |  |  |  |
|  | Mean | 6.79 | 3.31 |
|  | SD | 2.35 | 2.475 |
|  | Median | 7.63 | 2.67 |
|  | IQR | 5.14-8.52 | 1.21-4.98 |
|  | N | 100 | 299 |
| Validation |  |  |  |
|  | Mean | 6.76 | 3.42 |
|  | SD | 2.22 | 2.42 |
|  | Median | 7.16 | 2.88 |
|  | IQR | 5.46 - 8.61 | 1.35 - 5.08 |
|  | N | 102 | 298 |

Fig. 1

METHOD FOR DETERMINING RISK OF DIABETES

BACKGROUND

Diabetes mellitus is a serious illness characterized by a loss of the ability to regulate blood glucose levels. The American Diabetes Association addresses the diagnosis and classification of Diabetes in *Diabetes Care*, 32 (Suppl. 1): S62-S67 (2009) and *Diabetes Care*, 33 (Suppl. 1): S62-S69 (2010). The World Health Organization (WHO) estimates that more than 180 million people worldwide have Diabetes. This number is likely to more than double by 2030. In 2005, an estimated 1.1 million people died from Diabetes; this estimate likely undercounts deaths caused by Diabetes, as Diabetes contributes to other diseases, such as heart disease and kidney disease, that may be listed as the cause of death.

There is a need for new methods for identifying persons at risk of developing Diabetes.

SUMMARY

A method for calculating a diabetes risk score is provided. In one embodiment, the method comprises: a) measuring the levels of a plurality of biomarkers in a blood sample obtained from a human patient, wherein the plurality of biomarkers comprises at least five of the following biomarkers: glucose, adiponectin, CRP, IL2RA, ferritin, insulin and HbA1c; b) calculating a numerical score for the patient or categorizing the patient using the levels and, optionally, patient age and/or gender. The method may be performed using Formula I, or an alternative formula that provides results that are similar or identical to those obtained using Formula I, as determined by Spearman or chi-squared analysis on a human reference population.

$$D=X+0.062*Age-0.636*Gender+1.621*GLUCOSE-3.370*ADIPOQ+0.600*CRP+0.699*FTH1+1.350*IL2RA+0.491*INSULIN+0.259*HBA1C \quad \text{Formula I}$$

wherein:

X is any number, including 0, of any sign, and may have 0, 1, 2 or more than 2 decimal places, and in certain embodiments may be −23.114;

0.062*Age is patient age in years multiplied by 0.062;

0.636*Gender is patient gender, wherein female=0 and male=1, multiplied by 0.636;

1.621*GLUCOSE is the square root of the level of patient blood glucose in mg/dL, multiplied by 1.621;

3.370*ADIPOQ is the $\log_{10}$ of the level of patient blood adiponectin in µg/mL, multiplied by 3.370;

0.600*CRP is the $\log_{10}$ of level of patient blood CRP in mg/L, multiplied by 0.600;

0.699*FTH1 is the $\log_{10}$ of the level of patient blood ferritin in ng/mL, multiplied by 0.699;

1.350*IL2RA is the $\log_{10}$ of the level of patient blood IL2RA in U/mL, multiplied, by 1.350;

0.491*INSULIN is the $\log_{10}$ of the level of patient blood insulin in uIU/mL, multiplied 0.491; and 0.259*HBA1C is the level of patient blood Hb1Ac measured as a percentage of total hemoglobin in whole blood multiplied by 0.259.

In certain embodiments, the method may include: a) measuring the levels of a plurality of biomarkers in a blood sample obtained from the human subject, wherein said plurality of biomarkers comprises at least five of the following biomarkers: glucose, adiponectin, CRP, IL2RA, ferritin, insulin and HbA1c; and b) calculating a diabetes risk score for said subject using the levels and, optionally, subject age and/or gender, where the calculation is performed by a method selected from the group consisting of:

i) a first method wherein the levels of all said biomarkers are measured and calculating a diabetes risk score for the subjects using the levels using a first formula that is identical to Formula I; and ii) a second method comprising using measured levels of said at least five biomarkers and optional age and/or gender are used in calculating a diabetes risk score for a subject using a second formula;

wherein, when the first and second formulas of the first and second methods are applied to measured biomarker levels and optional age and/or gender for human reference population to generate first and second risk profiles, respectively, the second risk profile has a 95% confidence interval of the Spearman rank correlation coefficient squared ($R^2$) which is entirely above or includes a correlation value of 0.5 with the first risk profile.

In alternative embodiments, a method of categorizing the risk of developing a diabetic condition is provided. This method may comprise: a) measuring the levels of a plurality of biomarkers in a blood sample from a human subject, wherein the plurality of biomarkers comprises at least five of the following biomarkers: glucose, adiponectin, CRP, IL2RA, ferritin, insulin and HbA1c, and optionally subject age and/or gender, and; b) categorizing the subject into one of a plurality of mutually exclusive ordered risk categories wherein placement into the ordered risk categories is determined by a method selected from the group consisting of:

i) a first method comprising calculating a diabetes risk score for the subject using the levels using the Formula I; and categorizing the subject based on the calculated diabetes risk score into one of the plurality of mutually exclusive ordered risk categories that are each defined by a range of diabetes risk scores to provide the categorical risk assessment for the subject; and ii) a second method comprising using the measured levels of the at least five biomarkers and optional age and/or gender to categorize the subject into one of the plurality of mutually exclusive ordered risk categories in accordance with a risk profile to provide the categorical risk assessment for the subject, wherein when a plurality of categorical risk assessments from a human reference population calculated by the first method (first diabetes risk categorization) is compared to a plurality of categorical risk assessments from the human reference population calculated by the second method (second diabetes risk categorization), the second diabetes risk categorization is not independent with 95% confidence from the first diabetes risk categorization using a chi-squared test, and the ranges of the diabetes risk scores that define the plurality of ordered risk categories are selected such that the numbers of individuals from the human reference population in each risk category for both the first diabetes risk categorization and the second diabetes risk categorization are identical.

Computer readable medium comprising instructions for execution of the above-described algorithm, as well as kits containing the same, are also provided.

The foregoing summary is not intended to define every aspect of the invention, and additional aspects are described in other sections, such as the Detailed Description. The entire document is intended to be related as a unified disclosure, and it should be understood that all combinations of features described herein are contemplated, even if the combination of features are not found together in the same sentence, or paragraph, or section of this document.

In addition to the foregoing, the invention includes, as an additional aspect, all embodiments of the invention narrower in scope in any way than the variations specifically mentioned above. With respect to aspects of the invention described as a genus, all individual species are individually considered separate aspects of the invention. With respect to aspects described as a range, all sub-ranges and individual values are specifically contemplated.

BRIEF DESCRIPTION OF THE DRAWINGS

FIG. 1 provides a table showing descriptive statistics for the use of Algorithm A, as described in the Examples section of this disclosure.

DEFINITIONS

Figure 2:
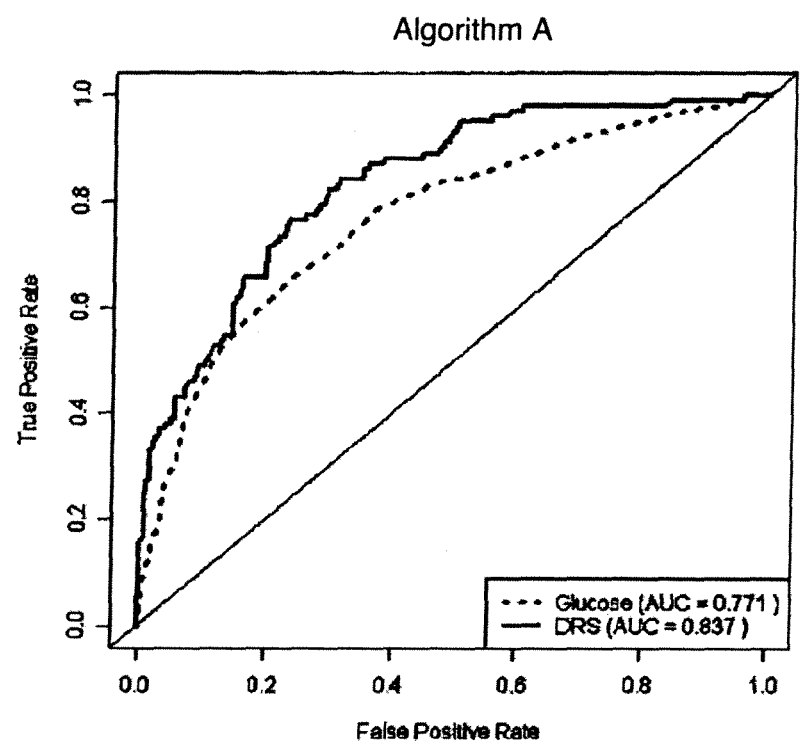
FIG. 2 show an ROC curve for Algorithm A.

The term "biomarker" in the context of this disclosure encompasses, without limitation, any measurable analyte, e.g., a protein, nucleic acid, metabolite, including a lipid metabolite, in a biological sample such as a bodily fluid, e.g., blood, obtained from a subject. Biomarkers can also include mutated proteins, mutated nucleic acids, splice variants, and modified proteins, e.g., glycosylated or phosphorylated proteins. Adiponectin (ADIPOQ), C-reactive protein (CRP); glucose (GLUCOSE); glutamic-pyruvate transaminase (GPT or ALT); glycosylated hemoglobin (HBA1C); heat shock 70 kDa protein 1B (HSPA1B); insulin-like growth factor binding protein 1 (IGFBP1); insulin-like growth factor binding protein 2 (IGFBP2); insulin (INS, INSULIN-M, pro-insulin and SCp), leptin (LEP) and triglycerides (TRIG) are examples of biomarkers. The biomarker GPT may be analyzed by measuring the GPT protein level or measuring the enzymatic activity as an alanine aminotransferase (ALT). The GPT enzymatic activity (ALT activity) may be measured using conventional methods known in the art. These markers are individually known; see US 2007/0218519 and US 2007/0259377, which are incorporated by reference herein in their entirety, for descriptions of the individual markers.

The term "clinical parameter" or "CP" encompasses all non-sample or non-analyte biomarkers of subject health status or other characteristics, such as, without limitation, age (AGE), race or ethnicity (RACE), gender (SEX), diastolic blood pressure (DBP) and systolic blood pressure (SBP), family history (FHX, including FHx1 for 1 parent and FHx2 for 2 parents), height (HT), weight (WT), waist (Waist) and hip (Hip) circumference, Waist-Hip ratio (WHr), body-mass index (BMI), past Gestational Diabetes Mellitus (GDM), and resting heart rate.

The term "diabetes" in the context of this disclosure encompasses Type 1 Diabetes, both autoimmune and idiopathic and Type 2 Diabetes (referred to herein as "Diabetes" or "T2DM"). The World Health Organization defined the diagnostic value of fasting plasma glucose concentration to 7.0 mmol/l (126 mg/dl) and above for Diabetes mellitus (whole blood 6.1 mmol/l or 110 mg/dl), or 2-hour glucose level greater than or equal to 11.1 mmol/L (greater than or equal to 200 mg/dL). It may also be possible to diagnose Diabetes based on an HbA1c level of greater than 6%, for instance, ≥6.5%. Other values suggestive of or indicating high risk for Diabetes mellitus include elevated arterial pressure greater than or equal to 140/90 mm Hg; elevated plasma triglycerides (greater than or equal to 1.7 mmol/L; 150 mg/dL) and/or low HDL-cholesterol (<0.9 mmol/L, 35 mg/dl for men; <1.0 mmol/L, 39 mg/dL women); central obesity (males: waist to hip ratio >0.90; females: waist to hip ratio>0.85) and/or body mass index exceeding 30 kg/m2; microalbuminuria, where the urinary albumin excretion rate greater than or equal to 20 μg/min or albumin:creatinine ratio greater than or equal to 30 mg/g).

The oral glucose tolerance test (OGTT) is principally used for diagnosis of Diabetes Mellitus when testing blood glucose levels are equivocal, during pregnancy, or in epidemiological studies (Definition, Diagnosis and Classification of Diabetes Mellitus and its Complications, Part 1, World Health Organization, 1999). The OGTT should be administered in the morning after at least 3 days of unrestricted diet (greater than 150 g of carbohydrate daily) and usual physical activity. A reasonable (30-50 g) carbohydrate-containing meal should be consumed on the evening before the test. The test should be preceded by an overnight fast of 8-14 hours during which water may be consumed. In some embodiments, the test is preceded by an overnight fast of no less than 10 hours After collection of the fasting blood sample, the subject should drink 75 g of anhydrous glucose or 82.5 g of glucose monohydrate in 250-300 ml of water over the course of 5 minutes. For children, the test load should be 1.75 g of glucose per kg body weight up to a total of 75 g of glucose. Timing of the test is from the beginning of the drink. Blood samples must be collected 2 hours after the test load. Diabetes over such a period unless otherwise enriched by other risk factors; in an unselected general population, the rate of conversion over such periods is typically estimated at 5-6%, or less than 1% per annum.

The term "gestational Diabetes" refers to glucose intolerance during pregnancy. This condition results in high blood sugar that starts or is first diagnosed during pregnancy.

"Diabetic condition" in the context of the present invention comprises type I and type II Diabetes mellitus, and pre-Diabetes (defined herein). It is also known in the art that Diabetic-related conditions include Diabetes and the pre-diabetic condition (defined herein).

The terms "formula," "algorithm," and "model" are used interchangeably for any mathematical equation, algorithmic, analytical or programmed process, or statistical technique that takes one or more continuous or categorical inputs (herein called "parameters") and calculates an output value, sometimes referred to as an "index", "index value", "category" or "risk category". Non-limiting examples of "formulas" include sums, ratios, and regression operators, such as coefficients or exponents, biomarker value transformations and normalizations (including, without limitation, those normalization schemes based on clinical parameters, such as gender, age, or ethnicity), decision trees, rules and guidelines, statistical classification models, and neural networks trained on historical populations. Of particular use for the biomarkers are linear and non-linear equations and statistical classification analyses to determine the relationship between levels of biomarkers detected in a subject sample and the subject's risk of Diabetes. In panel and combination construction, of particular interest are structural and synactic statistical classification algorithms, and methods of risk index construction, utilizing pattern recognition features, including established techniques such as cross-correlation, Principal Components Analysis (PCA), factor rotation, Logistic Regression (LogReg), Linear Discriminant Analysis (LDA), Eigengene Linear Discriminant Analysis (ELDA), Support Vector Machines (SVM), Random Forest (RF), Recursive Partitioning Tree (RPART), as well as other related decision tree classification techniques, Shruken Centroids (SC), StepAIC, Kth-Nearest Neighbor, Boosting, Decision Trees, Neural Networks, Bayesian Networks, Support Vector Machines, and Hidden Markov Models, Linear Regression or classification algorithms, Nonlinear Regression or classification algorithms, analysis of variants (ANOVA), hierarchical analysis or clustering algorithms; hierarchical algorithms using decision trees; kernel based machine algorithms such as kernel partial least squares algorithms, kernel matching pursuit algorithms, kernel Fisher's discriminate analysis algorithms, or kernel principal components analysis algorithms, among others. Many of these techniques are useful either combined with other selection techniques, such as forward selection, backwards selection, or stepwise selection, complete enumeration of all potential panels of a given size, genetic algorithms, or they may themselves include biomarker selection methodologies in their own technique. These may be coupled with information criteria, such as Akaike's Information Criterion (AIC) or Bayes Information Criterion (BIC), in order to quantify the tradeoff between additional biomarkers and model improvement, and to aid in minimizing overfit. The resulting predictive models may be validated in other studies, or cross-validated in the study they were originally trained in, using such techniques as Leave-One-Out (LOO) and 10-Fold cross-validation (10-Fold CV) or correlated to known predictive risk factors. A "DRS Formula" is a formula developed used to calculate a Diabetes risk score from inputs comprising the results from biomarker testing as described herein. A DRS Formula can be used to calculate a Diabetes risk score.

"Measuring" or "measurement" means assessing the presence, absence, quantity or amount (which can be an absolute or relative amount) of either a given substance within a clinical or subject-derived sample, including the derivation of qualitative or quantitative concentration levels of such substances, or otherwise evaluating the values or categorization of a subject's clinical parameters.

A "negative predictive value" or "NPV" is calculated by TN/(TN+FN) or the true negative fraction of all negative test results. It also is inherently impacted by the prevalence of the disease and pre-test probability of the population intended to be tested. See, e.g., O'Marcaigh A S, Jacobson R M, "Estimating The Predictive Value Of A Diagnostic Test, How To Prevent Misleading Or Confusing Results," Clin. Ped. 1993, 32(8): 485-491, which discusses specificity, sensitivity, and positive and negative predictive values of a test, e.g., a clinical diagnostic test. Often, for binary disease state classification approaches using a continuous diagnostic test measurement, the sensitivity and specificity is summarized by Receiver Operating Characteristics (ROC) curves according to Pepe et al, "Limitations of the Odds Ratio in Gauging the Performance of a Diagnostic, Prognostic, or Screening Marker," Am. J. Epidemiol 2004, 159 (9): 882-890, and summarized by the Area Under the Curve (AUC) or c-statistic, an indicator that allows representation of the sensitivity and specificity of a test, assay, or method over the entire range of test (or assay) cut points with just a single value. See also, e.g., Shultz, "Clinical Interpretation Of Laboratory Procedures," chapter 14 in Teitz, Fundamentals of Clinical Chemistry, Burtis and Ashwood (eds.), 4th edition 1996, W.B. Saunders Company, pages 192-199; and Zweig et al., "ROC Curve Analysis: An Example Showing The Relationships Among Serum Lipid And Apolipoprotein Concentrations In Identifying Subjects With Coronary Artery Disease," Clin. Chem., 1992, 38(8): 1425-1428. An alternative approach using likelihood functions, odds ratios, information theory, predictive values, calibration (including goodness-of-fit), and reclassification measurements is summarized according to Cook, "Use and Misuse of the Receiver Operating Characteristic Curve in Risk Prediction," Circulation 2007, 115: 928-935. Hazard ratios and absolute and relative risk ratios within subject cohorts defined by a test are a further measurement of clinical accuracy and utility. In this last, multiple methods are frequently used to defining abnormal or disease values, including reference limits, discrimination limits, and risk thresholds as per Vasan, "Biomarkers of Cardiovascular Disease: Molecular Basis and Practical Considerations," Circulation 2006, 113: 2335-2362.

Analytical accuracy refers to the repeatability and predictability of the measurement process itself, and may be summarized in such measurements as coefficients of variation, and tests of concordance and calibration of the same samples or controls with different times, users, equipment and/or reagents. These and other considerations in evaluating new biomarkers are also summarized in Vasan, Circulation 2006, 113: 2335-2362.

"Normal glucose levels" is used interchangeably with the term "normoglycemic" and "normal" and refers the definition published by the American Diabetes Association, currently a fasting venous plasma glucose concentration of less than 110 mg/dL. Although this amount is arbitrary, such values have been observed in subjects with proven normal glucose tolerance, although some may have IGT as measured by oral glucose tolerance test (OGTT). Glucose levels above normoglycemic are considered a pre-diabetic condition.

"Performance" is a term that relates to the overall usefulness and quality of a diagnostic or prognostic test, including, among others, clinical and analytical accuracy, other analytical and process characteristics, such as use characteristics (e.g., stability, ease of use), health economic value, and relative costs of components of the test. Any of these factors may be the source of superior performance and thus usefulness of the test.

"Positive predictive value" or "PPV" is calculated by TP/(TP+FP) or the true positive fraction of all positive test results. It is inherently impacted by the prevalence of the disease and pre-test probability of the population intended to be tested.

"Pre-Diabetes" or "pre-Diabetic," in the context of this disclosure indicates the physiological state, in an individual or in a population, and absent any prescribed therapeutic intervention (diet, exercise, pharmaceutical, or otherwise) of having a higher than normal expected rate of disease conversion to Diabetes Mellitus. Pre-Diabetes can also refer to those subjects or individuals, or a population of subjects or individuals who will, or are predicted to convert to Type 2 Diabetes Mellitus within a given time period (e.g., 5, 7 or 10 years) or time horizon at a higher rate than that of the general, unselected population. It may also be stated in terms of a relative risk from normal between quartiles of risk or as a likelihood ratio between differing biomarker and index scores, including those described herein.

In an unselected individual population, pre-Diabetes overlaps with, but is not necessarily a complete superset of, or contained subset within, all those with "pre-diabetic conditions" as many who will convert to Diabetes in a given time horizon are now apparently healthy, and with no obvious pre-diabetic condition, and many have pre-diabetic conditions but will not convert in a given time horizon; such is the diagnostic gap and need to be fulfilled by the invention.

"Diabetic condition" in the context of the present invention comprises type I and type II Diabetes mellitus, and pre-Diabetes (defined herein). It is also known in the art that Diabetic-related conditions include Diabetes and the pre-diabetic condition (defined herein).

"Pre-diabetic condition" refers to a metabolic state that is intermediate between normal glucose homeostasis and metabolism and states seen in frank Diabetes Mellitus. Pre-diabetic conditions include, without limitation, Metabolic Syndrome ("Syndrome X"), Impaired Glucose Tolerance (IGT), and Impaired Fasting Glycemia (IFG). IGT refers to post-prandial or post-OGTT abnormalities of glucose regulation, while IFG refers to abnormalities that are measured in a fasting state. The American Diabetes Association defines values for IFG as a fasting plasma glucose concentration of 4.4 mmol/L (100 mg/dL) or greater, but less than 7.0 mmol/L (126 mg/dL). Metabolic syndrome according to the National Cholesterol Education Program (NCEP) criteria are defined as having at least three of the following: blood pressure greater than or equal to 130/85 mm Hg; fasting plasma glucose greater than or equal to 6.1 mmol/L; waist circumference >102 cm (men) or >88 cm (women); triglycerides greater than or equal to 1.7 mmol/L; and HDL cholesterol <1.0 mmol/L (men) or 1.3 mmol/L (women). Many individuals with pre-diabetic conditions will not convert to T2DM.

"Risk" in the context of the present disclosure, relates to the probability that an event will occur over a specific time period, as in the conversion to frank Diabetes, and can mean a subject's "absolute" risk or "relative" risk. Absolute risk can be measured with reference to either actual observation post-measurement for the relevant time period, or with reference to index values developed from historical cohorts that have been followed for the relevant time period. Relative risk refers to the ratio of absolute risks of a subject compared either to the absolute risks of low risk cohorts or an average population risk, which can vary by how clinical risk factors are assessed. Odds ratios, the proportion of positive events to negative events for a given test result, are also commonly used (odds are according to the formula p/(1−p) where p is the probability of event and (1−p) is the probability of no event) to no-conversion. Alternative continuous measures which may be assessed in the context of the present invention include time to Diabetes conversion and therapeutic Diabetes conversion risk reduction ratios.

"Risk evaluation," or "evaluation of risk" in the context of the present invention encompasses estimating the probability, odds, or likelihood that an event or disease state may occur, the rate of occurrence of the event or conversion from one disease state to another, i.e., from a normoglycemic condition to a pre-diabetic condition or pre-Diabetes, or from a pre-diabetic condition to pre-Diabetes or Diabetes. Risk evaluation can also comprise prediction of future glucose, HBA1c scores or other indices of Diabetes, either in absolute or relative terms in reference to a previously measured population. The methods of the present invention may be used to make continuous or categorical measurements of the risk of conversion to Type 2 Diabetes. In the categorical scenario, the invention can be used to discriminate between normal and pre-Diabetes subject cohorts. In other embodiments, the present invention may be used so as to discriminate pre-Diabetes from Diabetes, or Diabetes from normal. Such differing use may require different biomarker combinations in individual panels, mathematical algorithm, and/or cut-off points, but be subject to the same aforementioned measurements of accuracy for the intended use.

A "sample" in the context of the present invention is a biological sample isolated from a subject and can include, by way of example and not limitation, whole blood, serum, plasma, blood cells, endothelial cells, tissue biopsies, lymphatic fluid, ascites fluid, interstitital fluid (also known as "extracellular fluid" and encompasses the fluid found in spaces between cells, including, inter alia, gingival crevicular fluid), bone marrow, cerebrospinal fluid (CSF), saliva, mucous, sputum, sweat, urine, or any other secretion, excretion, or other bodily fluids. "Blood sample" refers to whole blood or any fraction thereof, including blood cells, serum and plasma.

"Sensitivity" is calculated by TP/(TP+FN) or the true positive fraction of disease subjects.

"Specificity" is calculated by TN/(TN+FP) or the true negative fraction of non-disease or normal subjects.

By "statistically significant", it is meant that the alteration is greater than what might be expected to happen by chance alone (which could be a "false positive"). Statistical significance can be determined by any method known in the art. Commonly used measures of significance include the p-value, which presents the probability of obtaining a result at least as extreme as a given data point, assuming the data point was the result of chance alone. A result is often considered highly significant at a p-value of 0.05 or less.

The Spearman's rank correlation coefficient is calculated using known statistical procedures, e.g., using the formula:

$$\rho = 1 - \frac{6\sum d_i^2}{n(n^2 - 1)}$$

where $d_i = x_i - y_i =$ the difference between the ranks of corresponding values X, and $Y_i$, and n=the number of values in each data set (same for both sets). Spearman correlation coefficient is a standard statistical method and described in C. Spearman ("The proof and measurement of association between two things" Amer. J. Psychol., 15 (1904) pp. 72-101) and Corder ("Nonparametric Statistics for Non-Statisticians: A Step-by-Step Approach", Wiley, 2009).

Chi squared analysis is performed using known statistical procedures, such as any described in the following: Abramowitz et al ("Chapter 26", Handbook of Mathematical Functions with Formulas, Graphs, and Mathematical Tables, New York: Dover, 1965 ISBN 0-486-61272-4), NIST (Engineering Statistics Handbook—Chi-Square Distribution 2006), Johnson et al (Continuous Univariate Distributions (Second Ed., Vol. 1, Chapter 18). John Willey and Sons. 1994 ISBN 0-471-58495-9), Mood et al (Introduction to the Theory of Statistics 1974 Third Edition, p. 241-246, McGraw-Hill. ISBN 0-07-042864-6).

A "subject" or "patient" in the context of the present disclosure is a mammal. The mammal can be a human, non-human primate, mouse, rat, dog, cat, horse, or cow, but are not limited to these examples. Mammals other than humans can be used as subjects that represent animal models of Diabetes Mellitus, pre-Diabetes, or pre-diabetic conditions. A subject can be male or female. A subject can be one who has been previously diagnosed or identified as having Diabetes, pre-Diabetes, or a pre-diabetic condition, and optionally has already undergone, or is undergoing, a therapeutic intervention for the Diabetes, pre-Diabetes, or pre-diabetic condition. Alternatively, a subject can also be one who has not been previously diagnosed as having Diabetes, pre-Diabetes, or a pre-diabetic condition. For example, a subject can be one who exhibits one or more risk factors for Diabetes, pre-Diabetes, or a pre-diabetic condition, or a subject who does not exhibit Diabetes risk factors, or a subject who is asymptomatic for Diabetes, pre-Diabetes, or pre-diabetic conditions. A subject can also be one who is diagnosed, diagnosed or suffering from or at risk of developing Diabetes, pre-Diabetes, or a pre-diabetic condition.

"Traditional laboratory risk factors" or "TLRFs" correspond to biomarkers isolated or derived from subject samples and which are currently evaluated in the clinical laboratory and used in traditional global risk assessment algorithms, such as Stern, Framingham, Finland Diabetes Risk Score, ARIC Diabetes, and Archimedes. Traditional laboratory risk factors commonly tested from subject blood samples include, but are not limited to, total cholesterol (CHOL), LDL (LDL/LDLC), HDL (HDL/HDLC), VLDL (VLDLC), triglycerides (TRIG), glucose (including, without limitation, the fasting plasma glucose (Glucose) and the oral glucose tolerance test (OGTT)) and HBA1c (HBA1C) levels.

The oral glucose tolerance test (OGTT) is principally used for diagnosis of Diabetes Mellitus or pre-diabetic conditions when testing blood glucose levels are equivocal, during pregnancy, or in epidemiological studies (Definition, Diagnosis and Classification of Diabetes Mellitus and its Complications, Part 1, World Health Organization, 1999). The OGTT should be administered in the morning after at least 3 days of unrestricted diet (greater than 150 g of carbohydrate daily) and usual physical activity. A reasonable (30-50 g) carbohydrate-containing meal should be consumed on the evening before the test. The test should be preceded by an overnight fast of 8-14 hours, during which water may be consumed. After collection of the fasting blood sample, the subject should drink 75 g of anhydrous glucose or 82.5 g of glucose monohydrate in 250-300 ml of water over the course of 5 minutes. For children, the test load should be 1.75 g of glucose per kg body weight up to a total of 75 g of glucose. Timing of the test is from the beginning of the drink. Blood samples must be collected 2 hours after the test load. As previously noted, a diagnosis of impaired glucose tolerance (IGT) has been noted as being only 50% sensitive, with a >10% false positive rate, for a 7.5 year conversion to Diabetes when used at the WHO cut-off points. This is a significant problem for the clinical utility of the test, as even relatively high risk ethnic groups have only a 10% rate of conversion to Diabetes over such a period unless otherwise enriched by other risk factors; in an unselected general population, the rate of conversion over such periods is typically estimated at 5-6%, or less than 1% per annum.

DETAILED DESCRIPTION

In general terms, the method described herein provides diabetes risk scores that are very similar or identical to those obtained by the use of Formula I, where the similarity between scores are evaluated using a Spearman test or a chi-squared test on a human reference population, as described in greater detail below.

Formula I is as follows:

$$D = X + 0.062*Age - 0.636*Gender + 1.621*GLUCOSE - 3.370*ADIPOQ + 0.600*CRP + 0.699*FTH1 + 1.350*IL2RA + 0.491*INSULIN + 0.259*HBA1C$$

wherein:

X is any number, including 0, of any sign, and may have 0, 1, 2 or more than 2 decimal places, and in certain embodiments may be −23.114;

0.062*Age is patient age in years multiplied by 0.062;

0.636*Gender is patient gender, wherein female=0 and male=1, multiplied by 0.636;

1.621*GLUCOSE is the square root of the level of patient blood glucose in mg/dL, multiplied by 1.621;

3.370*ADIPOQ is the $\log_{10}$ of the level of patient blood adiponectin in μg/mL, multiplied by 3.370;

0.600*CRP is the $\log_{10}$ of level of patient blood CRP in mg/L, multiplied by 0.600;

0.699*FTH1 is the $\log_{10}$ of the level of patient blood ferritin in ng/mL, multiplied by 0.699;

1.350*IL2RA is the $\log_{10}$ of the level of patient blood IL2RA in U/mL, multiplied, by 1.350;

0.491*INSULIN is the $\log_{10}$ of the level of patient blood insulin in uIU/mL, multiplied 0.491; and 0.259*HBA1C is the level of patient blood Hb1Ac measured as a percentage of total hemoglobin in whole blood multiplied by 0.259.

In general terms, execution of Formula I produces a linear predictor, lp, that is related to group membership of a sample (e.g. case or controls), assuming a 50% prior probability of belonging to a group of converters being a case. This lp can be converted to a convenient score for an individual subject (DRS) on a 0-10 scale using the following equation:

$$DRS = 10 * e^{lp}/(1 + e^{lp})$$

This score correlates with the absolute risk of conversion at a specified prior probability (assuming a specified probability of 50%). Changing the prior probability that was used to construct the algorithm to a probability that reflects the actual percentage of "cases" in the population (based on epidemiology data of that population) effectively shifts the linear model by changing the intercept term, a, as follows:

$$a' = a + \ln(p_1/p_0)$$

Where a' is the new intercept, a is the intercept assuming a 50% prior, $p_1$ is the prior probability of being a case and $p_0$ is the prior probability of being a control. The remaining coefficients stay the same and a new linear predictor, lp', is computed. From this Risk (is computed as follows:

$$Risk = e^{lp'}/(1 + e^{lp'})$$

The Risk is the probability that a subject would become a case (a converter). For example, a risk of 25% indicates that 25% of the people with a similar DRS will convert to a diabetic within 5 years In certain embodiments, the method may include: a) measuring the levels of a plurality of biomarkers in a blood sample obtained from the human subject, wherein said plurality of biomarkers comprises at least five of the following biomarkers: glucose, adiponectin, CRP, IL2RA, ferritin, insulin and HbA1c; and b) calculating a diabetes risk score for said subject using the levels and, optionally, subject age and/or gender, where the calculation is performed by a method selected from the group consisting of:

i) a first method wherein the levels of all said biomarkers are measured and calculating a diabetes risk score for the subjects using the levels using a first formula that is identical to Formula I; and ii) a second method wherein measured levels of said at least five biomarkers and optional age and/or gender are used in calculating a diabetes risk score for a subject using a second formula;

wherein, when the first and second formulas of the first and second methods are applied to measured biomarker levels and optional age and/or gender for human reference population to generate first and second risk profiles, respectively, the second risk profile has a 95% confidence interval of the Spearman rank correlation coefficient squared ($R^2$) which is entirely above or includes a correlation value of 0.5 with the first risk profile.

In one embodiment, in order to determine if the first method provides results that are similar to those of the second method, a human reference population may be selected and two assays may be performed on the subjects of the population. In general terms, if the diabetes risk scores are expressed numerically (e.g., as a continuous variable) each subject will have two scores, then, for example, the scores for each method may be ranked across the population and compared using a Spearman test as described below. If the patients are categorized into one of a plurality of risk categories, then, for example, the patients may categorized into categories so that the ranges of the risk scores that define the second plurality of ordered risk categories are mutually exclusive relative to one another and cover the entire range of the second diabetes risk scores, b. the number of the second plurality of ordered risk categories is equal to the number of the first plurality of ordered risk categories, and c. the ranges of the risk scores that define the second plurality of ordered risk categories are selected such that the numbers of the patients in each risk category is identical to the numbers of the patients in each of the corresponding risk categories, in order of increasing risk, in the first plurality of ordered risk categories. The categorization may then be analyzed using a chi-squared test, as described below. Categorization may be done by first calculating a risk score, or in the absence of such a calculation.

In certain embodiments, the method may include: a) measuring the levels of a plurality of biomarkers in a blood sample obtained from a human patient, wherein the plurality of biomarkers comprises at least five of the following biomarkers: glucose, adiponectin, CRP, IL2RA, ferritin, insulin and HbA1c; b) calculating a diabetes risk score for the patient using the levels and, optionally, patient age and/or gender; and c) providing the diabetes risk score to the patient or the patient's healthcare practitioner in the form of a paper or electronic report; wherein steps a) and b), when performed on a human reference population, provide a first profile of diabetes risk scores having an absolute value of the 95% confidence interval of the Spearman correlation coefficient which is entirely above or includes a correlation value of 0.5 with a second profile of diabetes risk scores obtained from the plurality of human blood samples by: i. measuring the levels of glucose, adiponectin, CRP, IL2RA, ferritin, insulin and HbA1c in blood samples obtained from the plurality of human patients; and ii. calculating a second diabetes risk score for each of the patients using the levels using Formula I.

In alternative embodiments, the method may comprise: a) measuring the levels of a plurality of biomarkers in a blood sample from a human subject, wherein the plurality of biomarkers comprises at least five of the following biomarkers: glucose, adiponectin, CRP, IL2RA, ferritin, insulin and HbA1c, and optionally subject age and/or gender, and; b) categorizing the subject into one of a plurality of mutually exclusive ordered risk categories wherein placement into the ordered risk categories is determined by a method selected from the group consisting of:

i) a first method comprising calculating a diabetes risk score for the subject using the levels using the Formula I; and categorizing the subject based on the calculated diabetes risk score into one of the plurality of mutually exclusive ordered risk categories that are each defined by a range of diabetes risk scores to provide the categorical risk assessment for the subject; and ii) a second method comprising using the measured levels of the at least five biomarkers and optional age and/or gender to categorize the subject into one of the plurality of mutually exclusive ordered risk categories in accordance with a risk profile to provide the categorical risk assessment for the subject, wherein when a plurality of categorical risk assessments from a human reference population calculated by the first method (first diabetes risk categorization) is compared to a plurality of categorical risk assessments from the human reference population calculated by the second method (second diabetes risk categorization), the second diabetes risk categorization is not independent with 95% confidence from the first diabetes risk categorization using a chi-squared test, and the ranges of the diabetes risk scores that define the plurality of ordered risk categories are selected such that the numbers of individuals from the human reference population in each risk category for both the first diabetes risk categorization and the second diabetes risk categorization are identical.

In some embodiments, the method may include: a) measuring the levels of a plurality of biomarkers in a blood samples obtained from a human patient, wherein the plurality of biomarkers comprises at least five of the following biomarkers: glucose, adiponectin, CRP, IL2RA, ferritin, insulin and HbA1c, and; b) categorizing the patient into one of a first plurality of ordered risk categories using the levels and, optionally, patient age and/or gender to provide a categorical risk assessment for the patient; and c) providing the categorical risk assessment for the patient to the patient's healthcare practitioner in the form of a paper or electronic report; wherein steps a) and b), when performed on a human reference population, categorize the subjects of the human reference population among the ordered risk categories in a way that is not independent using a valid chi-squared test with 95% confidence from the categorization of the patients by: i. measuring the levels of glucose, adiponectin, CRP, IL2RA, ferritin, insulin and HbA1c in blood samples obtained from the plurality of human patients; and ii. calculating a second diabetes risk score for each of the patients using the levels using Formula I; and iii. categorizing each of the patients into one of a plurality of ordered risk categories that are each defined by a range of the risk scores to provide a second categorical risk assessment for each patient, as described above. In certain cases, the chi-squared analysis is performed with the following conditions: a. the ranges of the risk scores that define the second plurality of ordered risk categories are mutually exclusive relative to one another and cover the entire range of the second diabetes risk scores, b. the number of the second plurality of ordered risk categories is equal to the number of the first plurality of ordered risk categories, and c. the ranges of the risk scores that define the second plurality of ordered risk categories are selected such that the numbers of the patients in each risk category is identical to the numbers of the patients in each of the corresponding risk categories, in order of increasing risk, in the first plurality of ordered risk categories.

Methods for producing diabetes risk scores that are effectively very similar or identical to those provided by the use of Formula I (as evaluated by a Spearman or chi-squared test) without employing Formula I, include, for example: a) methods that measure the levels of one or more of the same biomarkers or clinical parameters using different units than those required by Formula I, e.g., by measuring any one or more of the following biomarkers: glucose, adiponectin, CRP, ferritin, IL2RA, insulin, and Hb1Ac in pounds/pint, moles/liter or some other unit of concentration, or by measuring age in days, months, or some other unit of time, for example; b) methods that multiply the levels of one or more of the same biomarkers by a coefficient that is similar to but not the same as the coefficients recited in Formula I (e.g., multiplying the age of a patient by 0.063 rather than 0.062, as required by Formula I); c) use of the same markers and clinical parameters as those required by Formula I, except that one or more of the markers is measured by a different method (e.g., using a different assay kit) and/or different instrumentation (e.g., using a different analyzer or chromatography system; d) methods that measure the levels of the same biomarkers using different normalization controls to those used by the kits described in the Examples section herein; e) use of the same markers and clinical parameters as those required by Formula I, except that one or more (e.g., one or two) of the markers recited in Formula I is substituted with another marker of equal prognostic value; f) methods that transform the levels or score non-linearly; g) use of the more markers and clinical parameters than those required by Formula I, where the additional markers have little or no prognostic value; h) use of a different value for X, the intercept that normalizes the other variables; i) using of a formula that is otherwise identical to that of Formula I, except the resultant risk score is on a different scale (e.g., on a scale of 1-100 as opposed to a scale of 1-10, etc.). The scale of the score may be derived using well known mathematical procedures, e.g., using the formula:

$$DRS = \exp(D)/(1+\exp(D)) * Y,$$

where DRS is the diabetes risk score, D is the output of the formula, and Y is the upper limit of the scale (e.g., 5, 10, 100, 1,000, etc).

In particular embodiments, a marker or clinical parameter not listed in Formula I may be employed in the method, either to substitute one or more markers or clinical parameters of Formula I, or in addition to the markers and clinical parameters listed in Formula I. Exemplary clinical parameters and biomarkers that could be employed in the method are set forth in the table that follows below, and in Table 1 of US20090012716, which Table is incorporated by reference for disclosure of those biomarkers and clinical parameters.

| Clinical Parameters | Biomarkers | Core Biomarkers I | Core Biomarkers II | Additional. Biomarkers I | Additional Biomarkers II |
|---|---|---|---|---|---|
| Age (AGE) Body Mass Index (BMI) Diastolic Blood Pressure (DBP) Family History (FHX) Gestational Diabetes Mellitus (GDM), Past Height (HT) Hip Circumference (Hip) Race (RACE) Sex (SEX) Systolic Blood Pressure (SBP) Waist Circumference (Waist) Weight (WT) | Cholesterol (CHOL) Glucose (fasting plasma glucose (FPG/Glucose) or with oral glucose tolerance test (OGTT)) HBA1c (Glycosylated Hemoglobin (HBA1/HBA 1C) High Density Lipoprotein (HDL/HDL C) Low Density Lipoprotein (LDL/LDLC) Very Low Density Lipoprotein (VLDLC) Triglycerides (TRIG) | Adiponectin (ADIPOQ) C-Reactive Protein (CRP) Fibrinogen alpha chain (FGA) Insulin, Pro-insulin, and soluble C-Peptide (any and/or all of which, INS) Leptin (LEP) | Advanced Glycosylation End Product-Specific Receptor (AGER) Alpha-2-HS-Glycoprotein (AHSG) Angiogenin (ANG) Apolipoprotein E (APOE) CD14 molecule (CD14) Ferritin (FTH1) Insulin-like growth factor binding protein 1 (IGFBP1) Interleukin 2 Receptor, Alpha (IL2RA) Vascular Cell Adhesion Molecule 1 (VCAM1) Vascular Endothelial Growth Factor (VEGF) Von Willebrand Factor (VWF) | Chemokine (C-C motif) ligand 2 aka monocyte chemoattractant protein-1 (CCL2) Cyclin-dependent kinase 5 (CDK5) Complement Component 3 (C3) Fas aka TNF receptor superfamily, member 6 (FAS) Hepatocyte Growth Factor (HGF) Interleukin 18 (IL18) Inhibin, Beta A aka Activin-A (INHBA) Resistin (RETN) Selectin-P (SELP) Tumor Necrosis Factor Receptor Superfamily, member 1B (TNFRSF1B) | Angiotensin-Converting Enzyme (ACE) Complement Component C4 (C4A) Complement Factor D (Adipsin) (CFD) Dipeptidyl-Peptidase 4 (CD26) (DPP4) Haptoglobin (HP) Interleukin 8 (IL8) Matrix Metallopeptidase 2 (MMP2) Selectin E (SELE) Tumor Necrosis Factor (TNF-Alpha) (TNF) Tumor Necrosis Factor Superfamily Member 1A (TNFRSF1A) |

In certain embodiments, the method may include measuring the blood levels of at least 4 of the following biomarkers: glucose, adiponectin, CRP, IL2RA, ferritin, insulin and HbA1c, e.g., measuring the levels glucose, adiponectin, CRP and HbA1c, and also measuring the levels of 1 or more other biomarkers which markers may be selected from the table shown above or Table 1 of US20090012716, for example. The total number of biomarkers measured in the method may be 4, 5, 6, 7, 8, 9, 10, 11, 12 or more then 12, more than 15, up to 20 or more. Likewise, the method may optionally employ the age and/or gender of the patient and, in certain cases, 1, 2, 3, 4, 5, or 6 or more, up to 10 or 20 clinical parameters such as the clinical parameters listed in the table shown above.

In certain cases, the method may employ coefficients in a range of coefficients and/or "adjusted coefficients" (i.e., coefficients that relative to the coefficients of Formula I, are adjusted to neutralize the effects of measuring biomarkers using units that are different to those recited in Formula I). As such, in certain cases, the method may comprise calculating a risk scores using Formula II:

$$D=b+(a1*glucose)-(a2*adiponectin)+(a3*CRP)+(a4*ferritin)+(a5*IL2RA)+(a6*insulin)+(a7*Hb1Ac);$$

where b is in the interval of −32.865 to −13.363;

a1*glucose is the square root of the level of blood glucose in mg/dL multiplied by a coefficient in the interval of 0.911 to 2.331 or an adjusted coefficient if the level of blood glucose is not measured in mg/dL;

a2*adiponectin is the $\log_{10}$ of the level of blood adiponectin in µg/mL multiplied by a coefficient in the interval of −5.419 to −1.321, or an adjusted coefficient if the level of blood adiponectin is not measured in µg/mL;

a3*CRP is the $\log_{10}$ of the level of blood CRP in mg/L multiplied by a coefficient in the interval of −0.094 to 1.294, or an adjusted coefficient if the level of blood adiponectin is not measured in mg/L;

a4*ferritin is the $\log_{10}$ of the level of blood Ferritin in ng/mL multiplied by a coefficient in the interval of −0.077 to 1.475, or an adjusted coefficient if the level of blood Ferritin is not measured in ng/mL;

a5*IL2RA is the $\log_{10}$ of the level of blood IL2RA in U/mL, multiplied by a coefficient in the interval of −1.132 to 3.832, or an adjusted coefficient if the level of blood IL2RA is not measured in U/mL;

a6*insulin is the $\log_{10}$ of the level of blood insulin in uIU/mL multiplied by a coefficient in the interval of −0.772 to 1.754, or an adjusted coefficient if the level of blood insulin is not measured in uIU/mL; and a7*Hb1Ac is the level of blood Hb1Ac measured in as a percentage of Hemoglobin in whole blood multiplied by a coefficient in the interval of −0.415 to 0.933, or an adjusted coefficient if the level of blood Hb1Ac is not measured as a percentage.

In certain cases, patient age may also be used as an input to Formula II, where the formula may further comprise the term+(a8*AGE), where a8*AGE is the age of the patient in years, multiplied by a coefficient in the interval of 0.071 to 1.107. Likewise, patient age may also be used as an input to Formula II, where the formula may further comprise the term+(a9*GENDER), where a9*GENDER is the gender of the patient, where a male=1 and female=0, multiplied by a coefficient in the interval of −1.353 to 0.081.

As noted above, the similarity between the risk scores obtained by the subject method and a method that employs Formula I for a human reference population may be evaluated using a Spearman test or a chi-squared test. In each of these tests (i.e., the Spearman and chi-squared tests), results obtained using the subject method are compared to the results obtained using a method that employs Formula I on the same patients. A human reference population is a population of human subjects of a size that allows the results to be significant to the required standard (e.g., at least 10, at least 25, at least 50, at least 100, at least 200, at least 500, at least 1000, at least 5000, at least 10,000 or more subjects). In certain cases, the subjects of the human reference population may be selected from a larger number of human subjects (e.g., at least 500, at least 1000, at least 5000, at least 10,000, at least 10,000, at least 100,000, or more subjects). In certain embodiments, the subjects of the human reference population may be may be randomly selected from the larger number of patients in order to remove bias from the test.

As noted above, in embodiments in which similarity between two methods in a human reference population is evaluated using a Spearman test, the diabetes risk scores for a number of subjects that is sufficient to provide results that are significant to the desired confidence level (e.g., risk scores for at least 25, at least 50, at least 100, at least 500, at least 200, at least 1,000, at least 10,000 or more patients) may be expressed as a continuous variable (e.g., a number with 0, 1, 2 or more decimal points), and the profile of the first diabetes risk scores (i.e., the profile of the risk scores obtained by use of Formula I) for the human reference population may have a 95% confidence interval of the Spearman rank correlation coefficient squared ($R^2$) which is entirely above or includes a correlation value of 0.5 (e.g., a Spearman rank correlation coefficient squared ($R^2$) which is entirely above or includes a correlation value of 0.55, a Spearman rank correlation coefficient squared ($R^2$) which is entirely above or includes a correlation value of 0.60, a Spearman rank correlation coefficient squared ($R^2$) which is entirely above or includes a correlation value of 0.70, a Spearman rank correlation coefficient squared ($R^2$) which is entirely above or includes a correlation value of 0.75, a Spearman rank correlation coefficient squared ($R^2$) which is entirely above or includes a correlation value of 0.80, a Spearman rank correlation coefficient squared ($R^2$) which is entirely above or includes a correlation value of 0.85, a Spearman rank correlation coefficient squared ($R^2$) which is entirely above or includes a correlation value of 0.90, a Spearman rank correlation coefficient squared ($R^2$) which is entirely above or includes a correlation value of 0.95, a Spearman rank correlation coefficient squared ($R^2$) which is entirely above or includes a correlation value of 0.97, a Spearman rank correlation coefficient squared ($R^2$) which is entirely above or includes a correlation value of 0.98, a Spearman rank correlation coefficient squared ($R^2$) which is entirely above or includes a correlation value of 0.99, a Spearman rank correlation coefficient squared ($R^2$) which is entirely above or includes a correlation value of 1.0) with a profile of second diabetes risk scores obtained from the reference population, where the second diabetes risk scores are obtained from the same subjects as the first diabetes risk score using an alternative but similar method.

In embodiments in which similarity between two methods in a human reference population is evaluated using a chi-squared test, the diabetes risk scores for a number of subjects that is sufficient to provide results that are significant to the desired confidence level (e.g., risk scores for at least 25, at least 50, at least 100, at least 500, at least 200, at least 1,000, at least 10,000 or more patients) are used to categorize the patients into a plurality of ordered risk categories (where in certain embodiments there are: a) two ordered risk categories such as "high" and "low" risk categories; b) three ordered risk categories such as "high", "medium" and "low" risk categories; c) four ordered risk categories such as "high", "medium-high", "medium-low" and "low" risk categories; or d) five or more ordered risk categories) such that each patient is assigned a categorical risk assessment (i.e., "high", "medium" or "low", etc.). In this embodiment, the categorization of the reference population among the ordered risk categories by the first diabetes risk scores is not independent using a valid chi-squared test with 95% confidence (e.g., not independent with 96% confidence, not independent with 97% confidence, not independent with 98% confidence, not independent with 99% confidence, or not independent with 100% confidence) from the categorization of the same subjects using Formula I, and then categorizing each of the patients into one of a second plurality of ordered risk categories that are each defined by a range of the risk scores to provide a second categorical risk assessment for each patient, wherein: a. the ranges of the risk scores that define the second plurality of ordered risk categories are mutually exclusive (i.e., non-overlapping) relative to one another and cover the entire range of the second diabetes risk scores, b. the number of the second plurality of ordered risk categories is equal to the number of the first plurality of ordered risk categories, and c. the ranges of the risk scores that define the second plurality of ordered risk categories are selected such that the numbers of the patients in each risk category is identical to the numbers of the patients in each of the corresponding risk categories, in order of increasing risk, in the first plurality of ordered risk categories. In other words, use of the subject method may provide a plurality of patients in each risk category, where the identities of the patients in each risk category are the same or very similar to the identities of the patients categorized into equivalent risk categories using Formula I.

The method may be performed on asymptomatic patients who may or may not be known to be at risk of diabetes, where risks include increased age, body mass index (BMI), family history, hypertension, and dyslipidemia, including patients that are insulin resistant, have altered beta cell function or are at risk of developing Diabetes based upon known clinical parameters or traditional laboratory risk factors, such as family history of Diabetes, low activity level, poor diet, excess body weight (especially around the waist), age greater than 45 years, high blood pressure, high levels of triglycerides, HDL cholesterol of less than 35, previously identified impaired glucose tolerance, previous Diabetes during pregnancy (Gestational Diabetes Mellitus or GDM) or giving birth to a baby weighing more than nine pounds, and ethnicity.

Measurement of Biomarkers

Methods for measuring the levels of the individual biomarkers employed in the subject method are either known or readily adapted from known methods. For example, blood glucose may be measured using conventional method using any of several commercially available kits. Adiponectin can be measured by any of several commercially available kits, including kits sold by Cayman Chemical (Ann Arbor, Mich.), Abnova Corporation (Taiwan) R & D systems (Minneapolis, Minn.). CRP can be measured by any of several commercially available kits, including kits from ALPCO (Salem, N.H.), Immuno-Biological Laboratories (Minneapolis, Minn.) and USBIO (Swampscott, Mass.). FTH1 can be measured by any of several commercially available kits, including a kit sold by Immuno-Biological Laboratories (Minneapolis, Minn.). IL2RA can be measured by any of several commercially available kits including kits sold by ALPCO (Salem, N.H.) and Bender MedSystems (Vienna, Austria). HBA1C can be measured by any of several commercially available kits including kits sold by Afinion (Oslo, Norway) and Diazyme (Poway, Calif.).

Biomarkers may be general measured in using several techniques designed to achieve predictable subject and analytical variability. On subject variability, many of the above biomarkers may be measured in a fasting state, and most commonly in the morning, providing a reduced level of subject variability due to both food consumption and metabolism and diurnal variation.

The actual measurement of levels of the markers can be determined at the protein level using any method known in the art. Such methods are well known in the art and include, e.g., immunoassays based on antibodies to proteins encoded by the genes, aptamers or molecular imprints, or other affinity reagents. Any biological material can be used for the detection/quantification of the protein or its activity. Alternatively, a suitable method can be selected to determine the activity of proteins encoded by the biomarker genes according to the activity of each protein analyzed.

The biomarkers can be detected in any suitable manner, and in certain embodiments may be detected by contacting a sample from the subject with an antibody which binds the biomarker and then detecting the presence or absence of a reaction product. The antibody may be monoclonal, polyclonal, chimeric, or a fragment of the foregoing, as discussed in detail above, and the step of detecting the reaction product may be carried out with any suitable immunoassay. The sample from the subject may be biological fluid, e.g., blood, as described above, and may be the same sample of biological fluid used to conduct the method described above.

Immunoassays may be homogeneous or heterogeneous. In a homogeneous assay the immunological reaction usually involves the specific antibody (e.g., anti-biomarker antibody), a labeled analyte, and the sample of interest. The signal arising from the label is modified, directly or indirectly, upon the binding of the antibody to the labeled analyte. Both the immunological reaction and detection of the extent thereof can be carried out in a homogeneous solution. Immunochemical labels which may be employed include free radicals, radioisotopes, fluorescent dyes, enzymes, bacteriophages, or coenzymes.

In a heterogeneous assay approach, the reagents are usually the sample, the antibody, and means for producing a detectable signal. Samples as described above may be used. The antibody can be immobilized on a support, such as a bead (such as protein A and protein G agarose beads), plate or slide, and contacted with the specimen suspected of containing the antigen in a liquid phase. The support is then separated from the liquid phase and either the support phase or the liquid phase is examined for a detectable signal employing means for producing such signal. The signal is related to the presence of the analyte in the sample. Means for producing a detectable signal include the use of radioactive labels, fluorescent labels, enzyme labels, or reporter reactions that produce a measurable signal. For example, if the antigen to be detected contains a second binding site, an antibody which binds to that site can be conjugated to a detectable group and added to the liquid phase reaction solution before the separation step. The presence of the detectable group on the solid support indicates the presence of the antigen in the test sample. Examples of suitable immunoassays include, but are not limited to oligonucleotides, immunoblotting, immunoprecipitation, immunofluorescence methods, chemiluminescence methods, electrochemiluminescence (ECL) or enzyme-linked immunoassays.

Those skilled in the art will be familiar with numerous specific immunoassay formats and variations thereof which may be useful for carrying out the method disclosed herein. See generally E. Maggio, Enzyme-Immunoassay, (1980) (CRC Press, Inc., Boca Raton, Fla.); see also U.S. Pat. No. 4,727,022 to Skold et al. titled "Methods for Modulating Ligand-Receptor Interactions and their Application," U.S. Pat. No. 4,659,678 to Forrest et al. titled "Immunoassay of Antigens," U.S. Pat. No. 4,376,110 to David et al., titled "Immunometric Assays Using Monoclonal Antibodies," U.S. Pat. No. 4,275,149 to Litman et al., titled "Macromolecular Environment Control in Specific Receptor Assays," U.S. Pat. No. 4,233,402 to Maggio et al., titled "Reagents and Method Employing Channeling," and U.S. Pat. No.

4,230,767 to Boguslaski et al., titled "Heterogeneous Specific Binding Assay Employing a Coenzyme as Label."

Antibodies can be conjugated to a solid support suitable for a diagnostic assay (e.g., beads such as protein A or protein G agarose, microspheres, plates, slides or wells formed from materials such as latex or polystyrene) in accordance with known techniques, such as passive binding. Antibodies as described herein may likewise be conjugated to detectable labels or groups such as radiolabels (e.g., 35S, 125I, 131I), enzyme labels (e.g., horseradish peroxidase, alkaline phosphatase), and fluorescent labels (e.g., fluorescein, Alexa, green fluorescent protein, rhodamine) in accordance with known techniques.

Antibodies can also be useful for detecting post-translational modifications of biomarkers, such as tyrosine phosphorylation, threonine phosphorylation, serine phosphorylation, glycosylation (e.g., O-GlcNAc). Such antibodies specifically detect the phosphorylated amino acids in a protein or proteins of interest, and can be used in immunoblotting, immunofluorescence, and ELISA assays described herein. These antibodies are well-known to those skilled in the art, and commercially available. Post-translational modifications can also be determined using metastable ions in reflector matrix-assisted laser desorption ionization-time of flight mass spectrometry (MALDI-TOF) (Wirth, U. et al. (2002) Proteomics 2(10): 1445-51).

For biomarkers known to have enzymatic activity, the activities can be determined in vitro using enzyme assays known in the art. Such assays include, without limitation, kinase assays, phosphatase assays, reductase assays, among many others. Modulation of the kinetics of enzyme activities can be determined by measuring the rate constant KM using known algorithms, such as the Hill plot, Michaelis-Menten equation, linear regression plots such as Lineweaver-Burk analysis, and Scatchard plot.

Tests to measure biomarkers can be implemented on a wide variety of diagnostic test systems. Diagnostic test systems are apparatuses that typically include means for obtaining test results from biological samples. Examples of such means include modules that automate the testing (e.g., biochemical, immunological, nucleic acid detection assays). Some diagnostic test systems are designed to handle multiple biological samples and can be programmed to run the same or different tests on each sample. Diagnostic test systems typically include means for collecting, storing and/or tracking test results for each sample, usually in a data structure or database. Examples include well-known physical and electronic data storage devices (e.g., hard drives, flash memory, magnetic tape, paper print-outs). It is also typical for diagnostic test systems to include means for reporting test results. Examples of reporting means include visible display, a link to a data structure or database, or a printer. The reporting means can be nothing more than a data link to send test results to an external device, such as a data structure, data base, visual display, or printer.

One embodiment of the present invention comprises a diagnostic test system that has been adapted to aide in the identification of individuals at risk of developing Diabetes. The test system employs means to apply a formula to inputs that include the levels of biomarkers measured from a biomarker panel in accordance with the description herein. In certain cases, test results from a biomarker panel of the present invention serve as inputs to a computer or microprocessor programmed with the formula. When the inputs include all the measurements of relevant biomarkers for a Diabetes risk score, then the diagnostic test system can include the score in the reported test results. If some factors apart from the biomarkers tested in the system are used to calculate the final risk score, then these factors can be supplied to the diagnostic test system so that it can complete the risk score calculation, or the formula can produce an index score that will be reported and externally combined with the other data to calculate a final risk score.

A number of diagnostic test systems are available for use in implementing the present invention and exemplify further means for carrying out the invention. One such device is the Abbott Architect® System, a high throughput, fully automated, clinical chemistry analyzer (ARCHITECT is a registered trademark of Abbott Laboratories, Abbott Park, Ill. 60064 United States of America, for data management and laboratory automation systems comprised of computer hardware and software for use in the field of medical diagnostics). The Architect® system is described at URL World-Wide-Web.abbottdiagnostics.com/pubs/2006/2006_AACC_Wilson_c16000.pdf (Wilson, C. et al., "Clinical Chemistry Analyzer Sub-System Level Performance," American Association for Clinical Chemistry Annual Meeting, Chicago, Ill., Jul. 23-27, 2006, and in Kisner H J, "Product development: the making of the Abbott ARCHITECT," Clin Lab Manage Rev. 1997 November-December; 11(6):419-21; Ognibene A et al., "A new modular chemiluminescence immunoassay analyser evaluated," Clin Chem Lab Med. 2000 March; 38(3):251-60; Park J W et al., "Three-year experience in using total laboratory automation system," Southeast Asian J Trop Med Public Health. 2002; 33 Suppl 2:68-73; Pauli D et al., "The Abbott Architect c8000: analytical performance and productivity characteristics of a new analyzer applied to general chemistry testing," Clin Lab. 2005; 51(1-2):31-41. Another useful system is the Abbott AxSYM® and AxSYM® Plus systems, which is described, along with other Abbott systems, at URL World-Wide-Web.abbottdiagnostics.com/Products/Instruments_by_Platform/.

Other devices useful for implementation of the tests to measure biomarkers are the Johnson & Johnson Vitros® system (VITROS is a registered trademark of Johnson & Johnson Corp., New Brunswick, N.J., United States of America, for medical equipment, namely, chemistry analyzer apparatus used to generate diagnostic test results from blood and other body fluids by professionals in hospitals, laboratories, clinics and doctor's offices), see URL World-Wide-Web.jnjgateway.com/home.jhtml?loc=USENG&page=menu&nodekey=/Prod_Info/Specialty/Diagnostics/Laboratory_and_Transfusion_Medicine/C hemistry_Immunodiagnostics; and the Dade-Behring Dimension® system (DIMENSION is a registered trademark of Dade Behring Inc., Deerfield Ill., United States of America for medical diagnostic analyzers for the analysis of bodily fluids, and computer hardware and computer software for use in operating the analyzers and for use in analyzing the data generated by the analyzers), see URL diagnostics.siemens.com/webapp/wcs/stores/selet/PSGenericDisplay~q_catalogId~e_-111~a_langId~e_-111~a_pageId~e_94489~a_storeId~e_10001.htm.

The biomarker tests can be carried out by laboratories such as those which are certified under the Clinical Laboratory Improvement Amendments of the United States (42 U.S.C. §263(a)), or other federal, national, state, provincial, or other law of any country, state, or province governing the operation of laboratories which analyze samples for clinical purposes. Such laboratories include, for example, Laboratory Corporation of America, with headquarters at 358 South Main Street, Burlington, N.C. 27215, United States of America; Quest Diagnostics, with corporate headquarters at 3 Giralda Farms, Madison, N.J. 07940, United States of America; and hospital-based reference laboratories and clinical chemistry laboratories. Suitable laboratories also include point of care laboratories.

Suitable sources for antibodies for the detection of biomarkers include commercially available sources such as, for example, Abazyme, Abnova, Affinity Biologicals, Antibody-Shop, Biogenesis, Biosense Laboratories, Calbiochem, Cell Sciences, Chemicon International, Chemokine, Clontech, Cytolab, DAKO, Diagnostic BioSystems, eBioscience, Endocrine Technologies, Enzo Biochem, Eurogentec, Fusion Antibodies, Genesis Biotech, GloboZymes, Haematologic Technologies, HyTest Ltd., Immunodetect, Immunodiagnostik, Immunometrics, Immunostar, Immunovision, Biogenex, Invitrogen, Jackson ImmunoResearch Laboratory, KMI Diagnostics, Koma Biotech, LabFrontier Life Science Institute, Lee Laboratories, Lifescreen, Maine Biotechnology Services, Mediclone, Mercodia, MicroPharm Ltd., ModiQuest, Molecular Innovations, Molecular Probes, Neoclone, Neuromics, New England Biolabs, Novocastra, Novus Biologicals, Oncogene Research Products, Orbigen, Oxford Biotechnology, Panvera, PerkinElmer Life Sciences, Pharmingen, Phoenix Pharmaceuticals, Pierce Chemical Company, Polymun Scientific, Polysiences, Inc., Promega Corporation, Proteogenix, Protos Immunoresearch, QED Biosciences, Inc., R&D Systems, Repligen, Research Diagnostics, Roboscreen, Santa Cruz Biotechnology, Seikagaku America, Serological Corporation, Serotec, SigmaAldrich, StemCell Technologies, Synaptic Systems GmbH, Technopharm, Terra Nova Biotechnology, TiterMax, Trillium Diagnostics, Upstate Biotechnology, US Biological, Vector Laboratories, Wako Pure Chemical Industries, and Zeptometrix. However, the skilled artisan can routinely make antibodies against any of the biomarkers employed in the method.

Reports

The methods of the present disclosure are suited for the preparation of a report that provides a risk score resulting from the method of the present disclosure. A "report," as described herein, is an electronic or tangible document which includes report elements that provide information of interest relating to a risk assessment and its results. A subject report includes at least a risk assessment, e.g., an indication as to the likelihood that a patient will become diabetic. A subject report can be completely or partially electronically generated, e.g., presented on an electronic display (e.g., computer monitor). A report can further include one or more of: 1) information regarding the testing facility; 2) service provider information; 3) patient data; 4) sample data; 5) an interpretive report, which can include various information including: a) indication; b) test data, where test data can include a normalized level of one or more genes of interest, and 6) other features.

The present disclosure thus provides for methods of creating reports and the reports resulting therefrom. The report may include a summary of the levels of biomarkers in the patient's blood. The report may include a score within a range of scores that indicate the risk of diabetes. The report may be presented in electronic format or on paper, and may be provided to the patient or the patient's healthcare provider.

In certain embodiments, the method disclosed herein can further include a step of generating or outputting a report providing the results of a subject response likelihood assessment, which report can be provided in the form of an electronic medium (e.g., an electronic display on a computer monitor), or in the form of a tangible medium (e.g., a report printed on paper or other tangible medium).

A report that includes information regarding the likelihood that a patient will develop diabetes may be provided to a user, e.g., a patient or a healthcare provider A person or entity who prepares a report ("report generator") may also perform the risk assessment. The report generator may also perform one or more of sample gathering, sample processing, and data generation, e.g., the report generator may also perform one or more of: a) sample gathering; b) sample processing; c) measuring a level of a test biomarker; d) measuring a level of a reference biomarkers; and e) determining a normalized level of a test biomarker. Alternatively, an entity other than the report generator can perform one or more sample gathering, sample processing, and data generation.

In certain embodiments, e.g., where the methods are completely executed on a single computer, the user or client provides for data input and review of data output. A "user" can be a health professional (e.g., a clinician, a laboratory technician, a physician (e.g., an oncologist, surgeon, pathologist), etc.).

In embodiments where the user only executes a portion of the method, the individual who, after computerized data processing according to the methods of the invention, reviews data output (e.g., results prior to release to provide a complete report, a complete, or reviews an "incomplete" report and provides for manual intervention and completion of an interpretive report) is referred to herein as a "reviewer." The reviewer may be located at a location remote to the user (e.g., at a service provided separate from a healthcare facility where a user may be located).

Where government regulations or other restrictions apply (e.g., requirements by health, malpractice, or liability insurance), all results, whether generated wholly or partially electronically, may be subjected to a quality control routine prior to release to the user.

The methods provided by the present disclosure may also be automated in whole or in part.

Computer-Based Systems and Methods

The methods and systems described herein can be implemented in numerous ways. In one embodiment of particular interest, the methods involve use of a communications infrastructure, for example the internet. Several embodiments are discussed below. It is also to be understood that the present method may be implemented in various forms of hardware, software, firmware, processors, or a combination thereof. The methods and systems described herein can be implemented as a combination of hardware and software. The software can be implemented as an application program tangibly embodied on a program storage device, or different portions of the software implemented in the user's computing environment (e.g., as an applet) and on the reviewer's computing environment, where the reviewer may be located at a remote site associated (e.g., at a service provider's facility).

For example, during or after data input by the user, portions of the data processing can be performed in the user-side computing environment. For example, the user-side computing environment can be programmed to provide for defined test codes to denote a likelihood "score," where the score is transmitted as processed or partially processed responses to the reviewer's computing environment in the form of test code for subsequent execution of one or more algorithms to provide a results and/or generate a report in the reviewer's computing environment. The score can be a numerical score (representative of a numerical value) or a non-numerical score representative of a numerical value or range of numerical values (e.g., "A" representative of a 90-95% likelihood of an outcome; "high" representative of a greater than 50% chance of response (or some other selected threshold of likelihood); "low" representative of a less than 50% chance of response (or some other selected threshold of likelihood); and the like.

The application program for executing the algorithms described herein may be uploaded to, and executed by, a machine comprising any suitable architecture. In general, the machine involves a computer platform having hardware such as one or more central processing units (CPU), a random access memory (RAM), and input/output (I/O) interface(s). The computer platform also includes an operating system and microinstruction code. The various processes and functions described herein may either be part of the microinstruction code or part of the application program (or a combination thereof) which is executed via the operating system. In addition, various other peripheral devices may be connected to the computer platform such as an additional data storage device and a printing device.

As a computer system, the system generally includes a processor unit. The processor unit operates to receive information, which can include test data (e.g., level of a response indicator gene product(s); level of a reference gene product(s); normalized level of a response indicator gene product(s)); and may also include other data such as patient data. This information received can be stored at least temporarily in a database, and data analyzed to generate a report as described above.

Part or all of the input and output data can also be sent electronically; certain output data (e.g., reports) can be sent electronically or telephonically (e.g., by facsimile, e.g., using devices such as fax back). Exemplary output receiving devices can include a display element, a printer, a facsimile device and the like. Electronic forms of transmission and/or display can include email, interactive television, and the like. In an embodiment of particular interest, all or a portion of the input data and/or all or a portion of the output data (e.g., usually at least the final report) are maintained on a web server for access, preferably confidential access, with typical browsers. The data may be accessed or sent to health professionals as desired. The input and output data, including all or a portion of the final report, can be used to populate a patient's medical record which may exist in a confidential database at the healthcare facility.

A system for use in the methods described herein generally includes at least one computer processor (e.g., where the method is carried out in its entirety at a single site) or at least two networked computer processors (e.g., where data is to be input by a user (also referred to herein as a "client") and transmitted to a remote site to a second computer processor for analysis, where the first and second computer processors are connected by a network, e.g., via an intranet or internet). The system can also include a user component(s) for input; and a reviewer component(s) for review of data, generated reports, and manual intervention. Additional components of the system can include a server component(s); and a database(s) for storing data (e.g., as in a database of report elements, e.g., interpretive report elements, or a relational database (RDB) which can include data input by the user and data output. The computer processors can be processors that are typically found in personal desktop computers (e.g., IBM, Dell, Macintosh), portable computers, mainframes, minicomputers, or other computing devices.

The networked client/server architecture can be selected as desired, and can be, for example, a classic two or three tier client server model. A relational database management system (RDMS), either as part of an application server component or as a separate component (RDB machine) provides the interface to the database.

In one example, the architecture is provided as a database-centric client/server architecture, in which the client application generally requests services from the application server which makes requests to the database (or the database server) to populate the report with the various report elements as required, particularly the interpretive report elements, especially the interpretation text and alerts. The server(s) (e.g., either as part of the application server machine or a separate RDB/relational database machine) responds to the client's requests.

The input client components can be complete, stand-alone personal computers offering a full range of power and features to run applications. The client component usually operates under any desired operating system and includes a communication element (e.g., a modem or other hardware for connecting to a network), one or more input devices (e.g., a keyboard, mouse, keypad, or other device used to transfer information or commands), a storage element (e.g., a hard drive or other computer-readable, computer-writable storage medium), and a display element (e.g., a monitor, television, LCD, LED, or other display device that conveys information to the user). The user enters input commands into the computer processor through an input device. Generally, the user interface is a graphical user interface (GUI) written for web browser applications.

The server component(s) can be a personal computer, a minicomputer, or a mainframe and offers data management, information sharing between clients, network administration and security. The application and any databases used can be on the same or different servers.

Other computing arrangements for the client and server(s), including processing on a single machine such as a mainframe, a collection of machines, or other suitable configuration are contemplated. In general, the client and server machines work together to accomplish the processing and reporting of the present method.

Where used, the database(s) is usually connected to the database server component and can be any device which will hold data. For example, the database can be a any magnetic or optical storing device for a computer (e.g., CDROM, internal hard drive, tape drive). The database can be located remote to the server component (with access via a network, modem, etc.) or locally to the server component.

Where used in the system and methods, the database can be a relational database that is organized and accessed according to relationships between data items. The relational database is generally composed of a plurality of tables (entities). The rows of a table represent records (collections of information about separate items) and the columns represent fields (particular attributes of a record). In its simplest conception, the relational database is a collection of data entries that "relate" to each other through at least one common field.

Additional workstations equipped with computers and printers may be used at point of service to enter data and, in some embodiments, generate appropriate reports, if desired. The computer(s) can have a shortcut (e.g., on the desktop) to launch the application to facilitate initiation of data entry, transmission, analysis, report receipt, etc. as desired.

Computer-Readable Storage Media

The present disclosure also contemplates an accessible computer-readable storage medium (e.g. a physical medium such as a CD-ROM, memory key, flash memory card, diskette, etc.) having stored thereon a program which, when executed in a computing environment, provides for implementation of algorithms to carry out all or a portion of the results of a method described herein. Where the computer-readable medium contains a complete program for carrying out a method described herein, the program includes program instructions for collecting, analyzing and generating output, and generally includes computer readable code devices for interacting with a user as described herein, processing that data in conjunction with analytical information, and generating unique printed or electronic media for that user. A file containing information may be "stored" on computer readable medium, where "storing" means recording information such that it is accessible and retrievable at a later date by a computer.

In certain embodiments, the computer readable medium may contain programming for execution of Formula I or an alternative formula that provides results that are similar or identical to those obtained using Formula I, as described above, after input of the variables, Where the storage medium provides a program which provides for implementation of a portion of the methods described herein (e.g., the user-side aspect of the methods (e.g., data input, report receipt capabilities, etc.)), the program provides for transmission of data input by the user (e.g., via the internet, via an intranet, etc.) to a computing environment at a remote site. Processing or completion of processing of the data is carried out at the remote site to generate a report. After review of the report, and completion of any needed manual intervention, to provide a complete report, the complete report is then transmitted back to the user as an electronic document or printed document (e.g., fax or mailed paper report). The storage medium containing a program according to the invention can be packaged with instructions (e.g., for program installation, use, etc.) recorded on a suitable substrate or a web address where such instructions may be obtained. The computer-readable storage medium can also be provided in combination with one or more reagents for carrying out response likelihood assessment (e.g., antibodies, supports, primers, probes, arrays, or other such kit components).

With respect to computer readable media, "permanent memory" refers to memory that is permanent. Permanent memory is not erased by termination of the electrical supply to a computer or processor. Computer hard-drive ROM (i.e. ROM not used as virtual memory), CD-ROM, floppy disk and DVD are all examples of permanent memory. Random Access Memory (RAM) is an example of non-permanent memory. A file in permanent memory may be editable and re-writable.

A "computer-based system" refers to the hardware means, software means, and data storage means used to analyze the information of the present invention. The minimum hardware of the computer-based system embodiment described herein contains a central processing unit (CPU), input means, output means, and data storage means. A skilled artisan can readily appreciate that any one of the currently available computer-based system are suitable for use in the present invention. The data storage means may comprise any manufacture comprising a recording of the present information as described above, or a memory access means that can access such a manufacture.

A "processor" references any hardware and/or software combination which will perform the functions required of it. For example, any processor herein may be a programmable digital microprocessor such as available in the form of a electronic controller, mainframe, server or personal computer (desktop or portable). Where the processor is programmable, suitable programming can be communicated from a remote location to the processor, or previously saved in a computer program product (such as a portable or fixed computer readable storage medium, whether magnetic, optical or solid state device based). For example, a magnetic medium or optical disk may carry the programming, and can be read by a suitable reader communicating with each processor at its corresponding station.

In certain embodiments, the processor will be in operable linkage, i.e., part of or networked to, the aforementioned device, and capable of directing its activities.

Kits

Kits for use in practicing certain methods described herein are also provided. In certain embodiments, a kit may include reagents for measuring the level of biomarkers, e.g., antibodies that may or may not be bound to a solid support, positive controls, negative controls, labeling reagents, and/or test strips, etc., and, in certain cases, a computer-readable medium as described above. In certain embodiments, the kits will further include instructions for practicing the subject method or means for obtaining the same (e.g., a website URL directing the user to a webpage which provides the instructions), where these instructions may be printed on a substrate, where substrate may be one or more of: a package insert, the packaging, reagent containers and the like. In the subject kits, the one or more components are present in the same or different containers, as may be convenient or desirable.

Utility

The method described herein may be used to make continuous or categorical measurements of the risk of conversion to Diabetes, thus diagnosing and defining the risk spectrum of a category of subjects defined as pre-diabetic.

Identifying the pre-diabetic subject enables the selection and initiation of various therapeutic interventions or treatment regimens in order to delay, reduce or prevent that subject's conversion to a diabetes disease state. Levels of an effective amount of biomarkers also allows for the course of treatment of Diabetes, pre-Diabetes or a pre-diabetic condition to be monitored. In this method, a biological sample can be provided from a subject undergoing treatment regimens or therapeutic interventions, e.g., drug treatments, for Diabetes. Such treatment regimens or therapeutic interventions can include, but are not limited to, exercise regimens, dietary modification, dietary supplementation, bariatric surgical intervention, administration of pharmaceuticals, and treatment with therapeutics or prophylactics used in subjects diagnosed or identified with Diabetes, pre-Diabetes, or a pre-diabetic condition. If desired, biological samples are obtained from the subject at various time points before, during, or after treatment.

The method can also be used to screen patient or subject populations in any number of settings. For example, a health maintenance organization, public health entity or school health program can screen a group of subjects to identify those requiring interventions, as described above, or for the collection of epidemiological data. Insurance companies (e.g., health, life, or disability) may screen applicants in the process of determining coverage or pricing, or existing clients for possible intervention. Data collected in such population screens, particularly when tied to any clinical progression to conditions like Diabetes, will be of value in the operations of, for example, health maintenance organizations, public health programs and insurance companies. Such data arrays or collections can be stored in machine-readable media and used in any number of health-related data management systems to provide improved healthcare services, cost effective healthcare, improved insurance operation, etc. See, for example, U.S. Patent Application No.; U.S. Patent Application No. 2002/0038227; U.S. Patent Application No. US 2004/0122296; U.S. Patent Application No. US 2004/0122297; and U.S. Pat. No. 5,018,067. Such systems can access the data directly from internal data storage or remotely from one or more data storage sites as further detailed herein. Thus, in a health-related data management system, wherein risk of developing a diabetic condition for a subject or a population comprises analyzing Diabetes risk factors, the present invention provides an improvement comprising use of a data array encompassing the biomarker measurements as defined herein and/or the resulting evaluation of risk from those biomarker measurements.

EXAMPLES

The following examples are set forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Celsius, and pressure is at or near atmospheric.

Example 1

Workflow and Sample Collection

The Diabetes Risk Test described below is a quantitative diagnostic test intended to aid in the assessment of a patient's risk for developing Type 2 diabetes within five years. The test is performed on a blood sample for patients at risk for diabetes.

The information provided by the Diabetes Risk Test may be used by a physician in conjunction with other clinical indicators to develop an effective diabetes prevention program. The Diabetes Risk Test may be indicated for use as an adjunctive test to complement, not replace, other diagnostic and clinical procedures.

The Diabetes Risk Test may be recommended for use in individuals who are known to be at risk of diabetes. Risks include increased age, body mass index (BMI), family history, hypertension, and dyslipidemia. Baseline samples from individuals 30 to 60 years of age who developed diabetes within 5 years and a random selection of controls were used to develop and independently validate the Diabetes Risk Score.

The Diabetes Risk Test requires fasting for a minimum of 10 hours prior to blood collection.

Blood is collected in an 8-10 mL red top serum tube or serum separator tube (SST). Allow to clot and separate serum within one hour of collection. Serum for the Diabetes Risk Test is stable for up to 7 days at 2-8° C.

Whole blood specimens are collected in a non-breakable collection tube containing EDTA. Whole blood samples for the Diabetes Risk Test are stable for up to 7 days at 2-8° C.

Sample Volume (preferred): 4-6 mL whole EDTA blood tube and 3-5 mL serum

Sample Volume (minimum): 2.0 mL whole EDTA blood tube and 1.0 mL serum

Samples should be shipped on the day of collection, using overnight delivery. Samples should be maintained at 2-8° C. or colder during shipping and storage. To ensure samples can be tested within the 7 days stability term, samples should be shipped overnight Monday through Thursday, and will be accepted for testing Monday through Friday during working hours (8 am to 5 µm Pacific Time).

The following individual tests are described in greater detail below.

| INSTRUMENT | ASSAY(S) |
|---|---|
| Randox Daytona | Glucose, hsCRP |
| Immulite 1000 | IL2Ra, Ferritin, Insulin |
| Bio-Rad D-10 | Hemoglobin A1c |
| SpectraMax ELISA | Adiponectin |
| Algorithm calculation | DP-PreDx |

Example 2

Glucose Assay Protocol

This example describes the procedure for testing patient samples for glucose using the Randox Daytona automated chemistry analyzer. The glucose test is intended for the in vitro determination of glucose concentration in serum.

The measurement of glucose in serum is enzymatic using both hexokinase (HK) and glucose-6-phosphate dehydrogenase (G6P-DH).

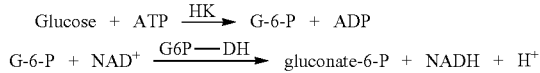

NADH is measured at 340 nm and is directly proportional to the amount of glucose in the sample.

Specimen Collection and Handling

Patient preparation: For fasting glucose, patient must fast for a minimum of 10 hours.

Collect blood in a red top serum tube or serum separator tube (SST). Allow to clot and separate serum within one hour of collection. Store and ship serum at 2-8° C. Serum glucose is stable for up to 7 days at 2-8° C. and up to 1 year frozen at ⁻20-⁻60° C.

Sample volume (preferred) 0.5 mL

Samples volume (minimum) 0.2 mL

Procedure

Blood glucose is measured using the Glucose (GLUC-HK) hexokinase method kit Cat. No. GL 3816 (Randox Laboratories Ltd, Oceanside, Calif.), according to GL 3816 Instructions for Use Revised 2009 Oct. 6 and Randox Daytona Operator Manual Version 1.6 Rev. May 2005

Results

Reference Range of blood glucose is 70-125 mg/dL

Critical high threshold of 500 mg/dL will trigger an alert in LIMS. Glucose results of 500 mg/dL or greater will be phoned immediately to provider and documented in the Orchard Harvest LIMS.

Critical low threshold of 45 mg/dL will trigger an alert in LIMS. Glucose results of 45 mg/dL or lower will be phoned immediately to provider and documented in the Orchard Harvest LIMS.

Reporting units: mg/dL

Reportable Range (linear range) 27 mg/dL to 630 mg/dL

Example 3

Adiponectin Assay Protocol

Adiponectin may be assayed using a kit supplied by Cayman Chemical (Ann Arbor, Mich.), Abnova Corporation (Taiwan), R & D systems (Minneapolis, Minn.), Mercodia (Sweden), or others.

Adiponectin is an adipocyte-secreted hormone, containing 244 amino acids with a molecular weight of approximately 30 kDa (28-30 kDa). It is one of the most abundant proteins in human blood, with circulating concentrations of 0.5-30 µg/ml, which accounts for approximately 0.01% of total plasma protein. Several manufacturers provide a method for the quantitative determination of human adiponectin in serum or plasma.

The Adiponectin ELISA used is a solid phase two-site enzyme immunoassay. It is based on the sandwich technique in which two monoclonal antibodies are directed against separate antigenic determinants on the adiponectin molecule. During incubation, adiponectin in the sample reacts with anti-adiponectin antibodies bound to the microtiter plate well. After washing, peroxidase conjugated anti-adiponectin antibodies are added and after the second incubation and a simple washing step that removes unbound enzyme labelled antibody, the bound conjugate is detected by reaction with 3,3',5,5'-tetramethylbenzidine (TMB). The reaction is stopped by adding acid to give a colorimetric endpoint that is read spectrophotometrically. The concentration of adiponectin in the sample is determined from the calibration curve run with the samples.

Specimen Collection and Handling

Collect blood in a red top serum tube or serum separator tube (SST). Allow to clot and separate serum within one hour of collection. Store and ship serum at 2-8° C. Serum Adiponectin is stable for up to 14 days at 2-8° C. For long term storage keep at −20° C. or below.

Sample volume (preferred) 0.2 mL
Sample volume (minimum) 0.1 mL

Procedure

Adiponectin is measured using the following protocol.
a. Prepare Enzyme Conjugate working solution by diluting the Enzyme Conjugate 11× with Enzyme Conjugate Buffer according to table 1 below. Mix gently. Diluted Enzyme Conjugate can be stored at 2-8° C. for two months.

TABLE 1

Enzyme Conjugate Dilution

| Number of strips | Volume Enzyme Conjugate 11X (µL) | Volume Enzyme Conjugate Buffer (mL) |
|---|---|---|
| 12 | 1 vial | 1 vial |
| 8 | 700 | 7 |
| 6 | 500 | 5 |
| 4 | 400 | 4 | b. Prepare Wash Buffer working solution by adding 800 mL deionized water to 40 mL Wash Buffer 21×, mix well. Diluted Wash Buffer can be stored at 2-8° C. for two months.
c. Prepare Sample Buffer working solution by adding 50 mL deionized water to 50 mL Sample Buffer 2×, mix well. Diluted Sample Buffer can be stored at 2-8° C. for two months.
d. Pipette 0.5 mL Sample Buffer into required number of 8-strip microtiter tubes or equivalent according to plate map.
e. Prepare a 1:101 dilution of samples and controls as follows: Add 5 µL sample to each well or tube containing 0.5 mL Sample Buffer according to the platemap (1:101 dilution). Seal plates and mix at 1350 rpm for 15 seconds on the Eppendorf thermomixer to thoroughly mix. Diluted samples can be sealed and stored at 2-8° C. up to 14 days.
f. Pipette 25 µL Calibrators and blanks into duplicate wells according to plate map.
g. Pipette 25 µL diluted samples and controls into duplicate wells according to plate map.
h. Pipette 100 µL Assay Buffer into each well. Seal plate with a plate sealer.
i. Transfer plate to plate shaker and adjust to 700 rpm. Incubate plate at room temperature (18-30° C.) while shaking for one hour.
j. During incubation, prepare BioTek plate washer by priming with Wash Buffer.
k. At end of one hour incubation, remove sealer from plate and transfer to BioTek plate washer. Select the Wash program: ELISA WASH 6×. Ensure that sufficient Wash Buffer is in the correct container. Press START to begin the BioTek wash cycle.
l. Pipette 100 µL Enzyme Conjugate into each well. Seal plate with a plate sealer.
m. Transfer plate to plate shaker and adjust to 700 rpm. Incubate plate at room temperature (C while shaking for one hour.
n. At end of one hour incubation, remove sealer from plate and transfer to BioTek plate washer. Select the Wash program: ELISA WASH 6×. Ensure that sufficient Wash Buffer is in the correct container. Press START to begin the BioTek wash cycle.
o. Pipette 200 µL Substrate TMB into each well. Seal plate and incubate for 15 minutes at room temperature (18-25° C.).
p. Remove sealer from plate and pipette 50 µL Stop Solution into each well. Shake plate gently by hand for 5 seconds to mix. Do not allow contents of wells to intermingle.
q. Transfer plate to Molecular Devices plate reader and read Optical Density (OD) at 450 nm within 30 minutes. Refer to TP-018: SpectraMax Operation and Maintenance for SpectraMax plate reader instructions.
r. The SpectraMax plate reader will calculate the concentration of adiponectin in the sample(s) in µg/mL.

Results

Results are reported in µg/mL. The reportable range (linear range) is 1.4 µg/mL to 33.2 µg/mL

Example 4

CRP Assay Protocol

This example describes the procedure for testing patient samples for high-sensitivity C-reactive protein (hs-CRP) using the Randox Daytona automated chemistry analyzer.

The hs-CRP test system is intended for the quantitative in vitro determination of C-reactive protein (CRP) in serum. C-reactive protein is present in the serum of normal individuals at levels between 0-5 mg/L. CRP levels at or near normal levels can be used for the assessment of cardiovascular event risk. CRP levels within or near the normal range may be affected by a number of different factors and should be interpreted along with clinical history.

Sample is reacted with a buffer and anti-CRP coated latex particles. The formation of the antibody-antigen complex results in an increase in turbidity, the extent of which is measured as the amount of light absorbed at 570 nm. By constructing a standard curve from the absorbance of the standards, CRP concentration of sample can be determined.

Specimen Collection and Handling

Patient preparation: For fasting hsCRP, patient must fast for a minimum of 10 hours. For non-fasting hsCRP no preparation is necessary.

Collect blood in a red top serum tube or serum separator tube (SST). Allow to clot and separate serum within one hour of collection. Store and ship serum at 2-8° C. Serum hsCRP is stable for up to 7 days at 2-8° C. and up to 6 months frozen at ⁻10-⁻30° C. Do not refreeze.

Sample volume (preferred) 0.5 mL
Samples volume (minimum) 0.2 mL

Procedure

CRP is measured using the hsCRP (GLUC-HK) Immunoturbidimetric method kit Cat. No. CP 3885 (Randox Laboratories Ltd, Oceanside, Calif.), using a minimum volume of 150 μL.

Results

Manufacturer's Reference Range is 0-5 mg/L for adults. Results are reported in mg/L, and the reportable (linear) range is 0.1 mg/L to 9.9 mg/L.

Example 5

Ferritin Assay Protocol

This example describes the procedure for testing patient serum samples for Ferritin using the Immulite 1000 automated chemistry analyzer.

Immulite 1000 Ferritin is a solid phase, two site chemiluminescent immunometric assay. Sample is added to a Test Unit containing one bead coated with murine monoclonal anti-Ferritin antibody. After incubation, alkaline phosphatase conjugated to goat polyclonal anti-Ferritin is added. Following incubation and washes, chemiluminescent substrate is added and light output is measured. The amount of light measured is directly proportional to the concentration of Ferritin in the sample.

This assay is intended for the quantitative measurement of Ferritin in serum as an aid in the clinical diagnosis of iron deficiency and overload.

The Ferritin molecule contains a protein shell (MW 450,000) and a core of iron. High concentrations are found in liver cells and in erythrocyte recycling centers (RE cells) of the liver, spleen and bone marrow. In these tissues, Ferritin serves as the body's principal storehouse for surplus iron, protecting against the toxic effects of excess and maintaining a readily mobilized reserve for erythropoieses.

Specimen Collection and Handling

Collect blood in a red top serum tube or serum separator tube (SST). Allow to clot and separate serum within one hour of collection. Store and ship serum at 2-8° C. Serum Ferritin is stable for up to 7 days at 2-8° C. and up to 2 weeks stored at −10° C. to −30° C.

Sample volume (preferred) 0.5 mL
Samples volume (minimum) 0.2 mL

Procedure

Ferretin is measured using the Immulite/Immulite 1000 Ferritin Cat. No. LKFE1 (100 tests) or LKFE5 (500 tests) (PILKFE-8, 2006-12-29; Siemens Medical Solutions Diagnostics Los Angeles, Calif.) assay on an Immulite 1000 analyzer (Siemens Medical Solutions Diagnostics Los Angeles, Calif.).

Results

Manufacturers Reference Range: Adult Male: 28-397 ng/mL, Adult Female: 6-159 ng/mL.

Reporting units are in ng/mL, and the Reportable Range (linear range) is 1.5 ng/mL to 1,500 ng/mL.

Example 6

IL2RA Assay Protocol

This example describes the procedure for testing patient serum samples for Interleukin-2 Receptor alpha (IL2Ra or IL2RA) using the Immulite 1000 automated chemistry analyzer.

Immulite 1000 IL2Ra is a solid-phase, two site chemiluminescent immunometric assay. Sample is added to a Test Unit containing one bead coated with murine monoclonal anti-IL2Ra antibody. After incubation, alkaline phosphatase conjugated to rabbit polyclonal anti-IL2Ra is added. Following incubation and washes, chemiluminescent substrate is added and light output is measured. The amount of light measured is directly proportional to the concentration of IL2Ra in the sample.

The receptor of the cytokine interleukin 2 (IL-2) plays a crucial role in the regulation of the immune response. Binding of Il-2 to its receptor (IL2R) on the surface of T-lymphocytes triggers a series of intracellular signaling events that results in the activation and proliferation of resting T cells and ultimately in the generation of helper, suppressor and cytotoxic T cells which mediate immune reactions.

The IL-2 receptor is made up of at least three distinct membrane components: the α chain (IL2Rα), the β chain (IL2Rβ), and the γ chain (IL2Rγ). Different combinations of these three components give rise to the generation of various forms of the IL2R, each of which manifests different binding affinities to IL2.

Most resting T cells, B cells, large granular lymphocytes and monocytes do not express significant numbers of this receptor on their surfaces. Upon activation, receptor molecules are expressed on the surface of the cells, and a soluble form (sIL2Ra) is released, which is about 10 kDa smaller than the membrane bound protein.

Specimen Collection and Handling

Collect blood in a red top serum tube or serum separator tube (SST). Allow to clot and separate serum within one hour of collection. Store and ship serum frozen. Serum IL2R is stable for up to 2 days at 2-8° C., for long term storage keep at −20° C. or below.

Sample volume (preferred) 0.5 mL
Samples volume (minimum) 0.2 mL

Procedure

IL2Ra is measured using an Immulite/Immulite 1000 IL2R assay Cat. No. LKIPZ (50 tests) LKIP1 (100 tests) LKIP5 (500 tests) (Immulite/Immulite 1000 IL2R) (PILKIP-16, 2007-04-10; Siemens Medical Solutions Diagnostics Los Angeles, Calif.) using an Immulite 1000 analyzer (Siemens Medical Solutions Diagnostics Los Angeles, Calif.).

Results

Results are reported in: U/mL, in the Reportable Range (linear range) of 50 U/mL to 7,500 U/mL.

Example 7

Insulin Assay Protocol

The example describes the procedure for testing patient serum samples for Insulin using the Immulite 1000 automated immunoassay system.

Immulite 1000 Insulin is a solid phase, two site chemiluminescent immunometric assay. This assay is intended for the quantitative measurement of Insulin in serum for the management of diabetes Sample is added to a Test Unit containing at least one bead coated with monoclonal murine anti-insulin. After incubation, alkaline phosphatase conjugated to polyclonal sheep anti-insulin is added. Following incubation and washes, chemiluminescent substrate is added and light output is measured. The amount of light measured is directly proportional to the concentration of Insulin in the sample.

Human insulin is a polypeptide hormone originating in the beta cells of the pancreas and serving as a principal regulator for the storage and production of carbohydrates. Its secretion is normally stimulated by increases in the amount of glucose in circulation. This leads to a higher insulin levels and more rapid tissue assimilation of glucose followed by a decline in the insulin level as the glucose level subsides.

Specimen Collection and Handling

Collect blood in a red top serum tube or serum separator tube (SST). Allow to clot and separate serum within one hour of collection. Store and ship serum at 2-8° C. Serum Insulin is stable for up to 7 days at 2-8° C. and 3 months at −20° C.

Sample volume (preferred) 1.0 mL

Samples volume (minimum) 0.5 mL

Procedure

Insulin is measured using an immulite 1000 Insulin assay Cat. No. LKIN1 (100 tests) or LKIN5 (500 tests) (Siemens Medical Solutions Diagnostics Los Angeles, Calif.) using an Immulite 1000 analyzer (Siemens Medical Solutions Diagnostics Los Angeles, Calif.).

Results

The Manufacturers Reference Range is 8.9 µIU/mL to 28.4 µIU/mL.

Results are reported in: µIU/mL, and the Reportable Range (linear range) is 2 to 300 µIU/mL.

Example 8

HBA1C Assay Protocol

This example describes the procedure for testing patient samples for Hemoglobin A1c (HbA1c) using the Bio-Rad D-10 automated high-performance liquid chromatography (HPLC) analyzer.

The D-10 Hemoglobin A1c program utilizes principles of ion-exchange high-performance chromatography (HPLC). Samples are automatically diluted on the D-10 and injected into the analytical cartridge. The D-10 delivers a programmed buffer gradient of increasing ionic strength to the cartridge, where the hemoglobins are separated based on their ionic interactions with the cartridge material. The separated hemoglobins then pass through the flow cell of the filter photometer, where changes in the absorbance at 415 nm are measured.

The D-10 software performs reduction of raw data from each analysis. Two-level calibration is used for quantitation of the HbA1c values. The A1c area is calculated using an exponentially modified Gaussian (EMG) algorithm that excludes the labile A1c and carbamylated peak areas from the A1c peak area.

The Bio-Rad D-10 Hemoglobin A1c Program is used for the determination of the percent of hemoglobin A1c in human whole blood.

The level of HbA1c is proportional to both the average glucose concentration and the life span of the red blood cell in the circulation.

Specimen Collection and Handling

Collect whole blood specimens in a non-breakable collection tube containing EDTA. Store and ship whole blood at 2-8° C. Whole blood samples may be stored for up to 7 days at 2-8° C.

Sample Volume (preferred): 4-6 mL whole EDTA blood tube

Sample Volume (minimum): 2.0 mL whole EDTA blood tube

Procedure

HBA1C is assayed using an Biorad D-10 Hemoglobin A1c assay, Cat. No. 220-0101 (Bio-Rad Laboratories, Hercules, Calif.)

Results

Manufacturers reference range in EDTA whole blood (non-pregnant individuals):

| HbA1c (%) | Glucose Control |
| --- | --- |
| >8 | Action suggested |
| <7 | Goal (American Diabetes Association) |
| <6 | Non-diabetic level |

Example 9

Validation of Diabetes Risk Score Algorithm

This example the results of the testing and analysis used to validate a Diabetes Risk Score (DRS) algorithm Study Objective The primary objective of the CLIA-001 study is to develop and validate an algorithm capable of estimating the five-year risk of developing diabetes from a panel of biomarkers in individuals. The algorithm includes concentration values of biomarkers and individual data (such as age and gender) demonstrating a significantly improved fit over a model with glucose alone and validated on a sequestered data set.

Summary of Validation

The algorithm were evaluated in the validation study. For the algorithm, markers were selected because their coefficients were statistically different from zero at the 90% confidence level (estimated using bootstrap resampling) in the training portion of the study. These markers are: age, gender, fasting plasma glucose, C-reactive protein (CRP), adiponectin (ADIPOQ) and ferritin (FTHI), glycated hemoglobin (HbA1c), insulin and interleukin receptor 2 alpha (IL2Ra).

The ability of the algorithm to predict risk of diabetes conversion was compared to the ability of the fasting glucose alone. For the final validation, the primary endpoint was improved fit as assessed by the likelihood ratio test. The secondary endpoint was improved discrimination as assessed by a Receiver Operator Characteristic (ROC) curve.

Algorithm A for the validation was:

$$D = -23.114 + 0.062*Age - 0.636*Gender + 1.621*GLUCOSE - 3.370*ADIPOQ + 0.600*CRP + 0.699*FTH1 + 1.350*IL2RA + 0.491*INSULIN + 0.259*HBA1C$$

(For Gender, female=0 and male=1)

$$DRS = (\exp(D)/(1+\exp(D)))*10$$

The above model was compared to a model based on fasting glucose alone using a likelihood ratio test. Deviance for the validation data was calculated with the following model estimated from 10,000 bootstrap replicates of the training data:

$$Glucose\_Score = -23.227 + 2.291*GLUCOSE$$

The algorithm must fit the data significantly better ($p<0.025$) than the glucose-alone model based on a likelihood ratio test adjusted for the degrees of freedom in the model.

Summary of Results

The algorithms met both the primary and secondary endpoints. The primary endpoint was superior fit to glucose alone based on the Likelihood Ratio test. The secondary endpoint was a comparison of ROC curves (by the method of DeLong, DeLong and Clarke-Pearson, as implemented in the ucR package for the R statistical computer language).

Detailed Results a. Data Exclusions

A total of 686 measurements of ALT were below the limit of quantification of the assay. ALT was removed from subsequent analysis. All 800 samples were quantitatively detected across the remaining 4 assays with the exception of 34 out of range in CRP and 1 out of range in FTH1. Values at the limit of detection were set to the limit value. All samples except sample ID 89992477 (PID 097075) and sample ID 89992478 (PID 097145) were included in subsequent analysis.

b. Algorithm Validation

Data Preparation

Predictor values were transformed by taking the log, square root or square of the raw concentrations if the distribution of the transformed values more closely approximated the normal distribution. The independence of the predictors was assessed based on their correlation to each other; none were highly correlated as defined in the statistical analysis plan ($R>0.7$). In addition, a linearity evaluation was performed and all quantitative metrics appeared linearly and significantly related to outcome.

Determination of Model Parameters

A weighted (prior probability of conversion=50%) logistic regression model was used to balance sensitivity and specificity. Coefficients were estimated for the selected markers on 10,000 bootstrap replicates. The algorithm utilizes the median value of these replicates.

Score is calculated as $DRS = \exp(lp)/(1+\exp(lp))*10$ (where lp is the linear sum of the products of each biomarker and its respective coefficient Risk is calculated as follows Ip is adjusted from a 50% prior to the test population prior using the equation:

$$lp' = lp + \log(p/(1-p))$$

where p is the proportion of expected 5 year converters in the test population $$Risk = \exp(lp')/(1+\exp(lp'))$$

D=lp.

Likelihood Ratio Test

The DRS Algorithm was compared to a model of fasting glucose alone using a likelihood ratio test.

Comparison of ROC Curves

ROC curves were calculated for each algorithm and for Fasting Glucose alone. These results are shown in FIG. 2

Data Transformation

To improve the symmetry of the distributions Log10 transformations were used for insulin, IL2Ra, ADIPOQ, CRP, and FTHI. Glucose was transformed with a square root while age was left raw. Gender was coded as 0=female, 1=male.

CONCLUSIONS

Algorithm A, as shown below:

$$D = -23.114 + 0.062*Age - 0.636*Gender + 1.621*GLUCOSE - 3.370*ADIPOQ + 0.600*CRP + 0.699*FTH1 + 1.350*IL2RA + 0.491*INSULIN + 0.259*HBA1C$$

met all acceptance criteria. Specifically, Algorithm A performed better ($p<1e-5$) than fasting glucose alone, based on the results of a likelihood ratio test. Algorithm A will provide an accurate prediction of risk of diabetes in people between thirty and sixty years of age.

What is claimed is:

1. A method of preventing development of diabetes in a subject, comprising:
    a) measuring levels of a plurality of biomarkers in a blood sample obtained from the human subject, wherein said plurality of biomarkers comprises at least five of the following biomarkers: glucose, adiponectin, CRP, IL2RA, ferritin, insulin and HbA1c;
    b) calculating a diabetes risk score for said subject as a function of said measured levels and optionally, the subject's age and/or gender;
    c) applying the function of measured biomarker levels and optional age and/or gender of the subject to measured biomarker levels and optional age and/or gender of a human reference population to generate a risk profile associated with the reference population, the risk profile has a 95% confidence interval of a Spearman rank correlation coefficient squared ($R^2$) that is entirely above or includes a correlation value of 0.5 with a comparative risk profile associated with the reference population generated from the formula:

$$D = X + 0.062*Age - 0.64*Gender + 1.62*GLUCOSE - 3.37*ADIPOQ + 0.60*CRP + 0.70*FTH1 + 1.35*IL2RA + 0.49*INSULIN + 0.26*HBA1C,$$

wherein:
  0.062*Age is subject age in years multiplied by 0.062;
  0.64*Gender is subject gender, wherein female=0 and male=1, multiplied by 0.64;
  1.62*GLUCOSE is the square root of the level of subject blood glucose in mg/dL, multiplied by 1.62;
  3.37*ADIPOQ is the log10 of the level of subject blood adiponectin in μg/mL, multiplied by 3.37;
  0.60*CRP is the log10 of level of subject blood CRP in mg/L, multiplied by 0.60;
  0.70*FTH1 is the log10 of the level of subject blood level ferritin in ng/mL, multiplied by 0.70;
  1.35*IL2RA is the log10 of the level of subject blood IL2RA in U/mL, multiplied by 1.35;
  0.49*INSULIN is the log10 of the level of subject blood insulin in ulU/mL, multiplied by 0.49;

0.26*HBA1C is the level of subject blood Hb1Ac measured in as a percentage of total hemoglobin in blood multiplied by 0.26; and X is any number.

2. The method of claim 1, wherein said human reference population comprises at least 25 subjects.

3. The method of claim 1, wherein the subjects of said human reference population are randomly chosen from a larger population of human subjects.

4. The method of claim 1, further comprising: initiating a therapeutic intervention or a treatment regimen to delay, reduce or prevent the human subject's conversion to a diabetes disease state is performed if the calculated diabetes risk score indicates a risk that the subject has a high risk of developing diabetes.

5. The method of claim 1, further comprising: initiating a therapeutic intervention or a treatment regimen to delay, reduce or prevent the human subject's conversion to a diabetes disease state is performed if the calculated diabetes risk score indicates a risk that the subject has a moderate risk of developing diabetes.

6. A method of preventing a human subject from developing diabetes if a categorical risk assessment associated with the human subject falls within a high risk mutually exclusive ordered risk category or a moderate risk mutually exclusive ordered risk category from among a plurality of mutually exclusive ordered risk categories consisting of high risk, moderate risk and low risk, comprising:

a) measuring levels of a plurality of biomarkers in a sample obtained from the human subject, wherein said plurality of biomarkers comprises at least five of the following biomarkers: glucose, adiponectin, CRP, IL2RA, ferritin, insulin and HbA1c;

b) generating a categorical risk assessment associated with the human subject generated as a function of a diabetes risk score (D) using said measured levels and optionally, the subject's age and/or gender by the formula:

$$D = X + 0.062*\text{Age} - 0.64*\text{Gender} + 1.62*\text{GLUCOSE} - 3.37*\text{ADIPOQ} + 0.60*\text{CRP} + 0.70*\text{FTH1} + 1.35*\text{IL2RA} + 0.49*\text{INSULIN} + 0.26*\text{HBA1C},$$

wherein:

0.062*Age is subject age in years multiplied by 0.062;

0.64*Gender is subject gender, wherein female=0 and male=1, multiplied by 0.64;

1.62*GLUCOSE is the square root of the level of subject blood glucose in mg/dL, multiplied by 1.62;

3.37*ADIPOQ is the log10 of the level of subject blood adiponectin in µg/mL, multiplied by 3.37;

0.60*CRP is the log10 of level of subject blood CRP in mg/L, multiplied by 0.60;

0.70*FTH1 is the log10 of the level of subject blood level ferritin in ng/mL, multiplied by 0.70;

1.35*IL2RA is the log10 of the level of subject blood IL2RA in U/mL, multiplied by 1.35;

0.49*INSULIN is the log10 of the level of subject blood insulin in uIU/mL, multiplied by 0.49;

0.26*HBA1C is the level of subject blood Hb1Ac measured in as a percentage of total hemoglobin in blood multiplied by 0.26; and X is any number, wherein when a plurality of categorized risk assessments from a plurality of human subjects calculated as a function of the formula is compared to a plurality of comparative categorized risk assessments from a human reference population each generated as a function of levels of at least five of: glucose, adiponectin, CRP, IL2RA, ferritin, insulin and HbA1c associated with each human reference population subject, and optionally each human reference population subject's age and/or gender, the plurality of comparative categorized risk assessments from the human reference population:

is not independent with 95% confidence, using a chi-squared test, from the categorical risk assessments generated as a function of the formula, and each mutually exclusive ordered risk category includes a range of diabetes risk scores (D) selected such that each individual mutually exclusive ordered risk category generated by the formula includes an identical number of human subjects as a number of human reference population subjects included in a corresponding mutually exclusive ordered risk category generated as a function of the levels of at least five of: glucose, adiponectin, CRP, IL2RA, ferritin, insulin and HbA1c associated with each human reference population subject, and optionally each human reference population subject's age and/or gender.

7. The method of claim 6, wherein said subject is categorized into one of said risk categories using at least the levels of glucose, adiponectin, CRP and HbA1c in the blood of said subject, and subject age.

8. The method of claim 6, wherein said human reference population comprises at least 25 subjects.

9. The method of claim 6, wherein the subjects of said human reference population are randomly chosen from a larger population of human subjects.

10. The method of claim 6, further comprising:

c) initiating a therapeutic intervention or a treatment regimen to delay, reduce or prevent the human subject's conversion to a diabetes disease state if the calculated diabetes risk score indicates a risk that the subject will develop diabetes.

11. The method of claim 6, further comprising:

c) initiating a therapeutic intervention or a treatment regimen to delay, reduce or prevent the human subject's conversion to a diabetes disease state if the calculated diabetes risk score indicates a high risk or moderate risk that the subject will develop diabetes.

* * * * *